(12) United States Patent
Stehr et al.

(10) Patent No.: US 9,909,166 B2
(45) Date of Patent: Mar. 6, 2018

(54) METHOD AND KIT FOR THE DETECTION OF NUCLEIC ACIDS

(71) Applicant: GNA BIOSOLUTIONS GMBH, Planegg (DE)

(72) Inventors: Joachim Stehr, Planegg (DE); Federico Buersgens, Planegg (DE); Lars Ullerich, Planegg (DE)

(73) Assignee: GNA Biosolutions GmbH, Planegg (DE)

( * ) Notice: Subject to any disclaimer, the term of this patent is extended or adjusted under 35 U.S.C. 154(b) by 261 days.

(21) Appl. No.: 14/385,428

(22) PCT Filed: Mar. 14, 2013

(86) PCT No.: PCT/EP2013/055250
§ 371 (c)(1),
(2) Date: Sep. 15, 2014

(87) PCT Pub. No.: WO2013/135820
PCT Pub. Date: Sep. 19, 2013

(65) Prior Publication Data
US 2015/0184234 A1    Jul. 2, 2015

(30) Foreign Application Priority Data
Mar. 14, 2012   (DE) .................. 10 2012 203 964

(51) Int. Cl.
*C12Q 1/68* (2006.01)
*C07H 21/00* (2006.01)
*G06F 19/10* (2011.01)

(52) U.S. Cl.
CPC .......... *C12Q 1/6818* (2013.01); *C12Q 1/682* (2013.01); *C12Q 1/6816* (2013.01); *C12Q 1/6834* (2013.01); *G06F 19/10* (2013.01)

(58) Field of Classification Search
CPC .......... C12Q 1/68; C12Q 1/6813; C07H 21/00
See application file for complete search history.

(56) References Cited

U.S. PATENT DOCUMENTS 6,225,061 B1 *  5/2001  Becker .................... B01J 19/16
                                                   159/1.1
6,812,334 B1  11/2004  Mirkin et al.
(Continued)

FOREIGN PATENT DOCUMENTS

| EP | 1870478 | 12/2007 |
|---|---|---|
| WO | WO 2004/083902 A2 | 9/2004 |
| WO | WO 2005/071115 A1 | 8/2005 |

OTHER PUBLICATIONS

Kennedy et al.,Locked nucleic acids for optimizing displacement probes for quantitative real-time PCR. Analytical Biochemistry 348 : 294 (2006).*
(Continued)

*Primary Examiner* — Ethan C Whisenant
(74) *Attorney, Agent, or Firm* — Hodgson Russ LLP

(57) ABSTRACT

Method for the determination of the concentration of a type of specific nucleic acids (10) in a sample, wherein the sequences of the specific nucleic acid (10) at least partially match a reference sequence, and/or for the determination of the degree of the match of the sequences of specific nucleic acids (10) of a type in a sample (9) and a reference sequence, comprising the following steps: providing a first probe (1), which possesses a first oligonucleotide (3) on its surface; providing a second oligonucleotide (7), which is partially complementary to the first oligonucleotide (3) or to a first oligonucleotide adapter (20), which is partially complementary to the first oligonucleotide (3), and wherein the second oligonucleotide (7) is partially complementary to the reference sequence; combining of the first probe (1) and the second oligonucleotide (7) and—if applicable—the first (Continued)

oligonucleotide adapter (20) with the sample (9), wherein a specific nucleic acid (10) contained in the sample (9) can hybridize with the second oligonucleotide (7) and the second oligonucleotide (7) is activated by the hybridization.

14 Claims, 18 Drawing Sheets

(56) References Cited

U.S. PATENT DOCUMENTS

| | | | | |
|---|---|---|---|---|
| 7,960,357 | B2* | 6/2011 | Dirks | 435/6.11 |
| 2003/0235837 | A1* | 12/2003 | Keim | C12Q 1/689 435/6.15 |
| 2005/0277125 | A1* | 12/2005 | Benn | B01J 19/0046 435/6.11 |
| 2005/0287548 | A1 | 12/2005 | Bao et al. | |
| 2006/0127940 | A1* | 6/2006 | Bao | C12Q 1/6818 435/6.11 |
| 2008/0261205 | A1* | 10/2008 | Denomme | C07H 21/00 435/6.16 |
| 2010/0075335 | A1 | 3/2010 | Tavares et al. | |
| 2010/0201381 | A1 | 8/2010 | Iqbal et al. | |
| 2010/0279305 | A1* | 11/2010 | Kuersten | C12Q 1/6855 435/6.16 |
| 2011/0104676 | A1* | 5/2011 | Pierce | C12Q 1/682 435/6.11 |
| 2012/0088691 | A1* | 4/2012 | Chen | B01L 7/52 506/12 |
| 2012/0315623 | A1* | 12/2012 | Alocilja | B82Y 15/00 435/5 |
| 2014/0272972 | A1* | 9/2014 | Lee | C12Q 1/682 435/6.11 |

OTHER PUBLICATIONS

Niu et al., Enzyme-enhanced fluorescence detection of DNA on etched optical fibers. Biosensors and Bioelectronics 24: 2943 (2009).*
Brown et al. Molecular beacons attached to glass beads fluoresce upon hybridisation to target DNA. Chemical Communications p. 621 (2000).*
Dirks et al., Triggered amplification by hybridization chain reaction. PNAS 101(43): 15275 (2004).*
Du et al.,Hybridization-Based Unquenching of DNA Hairpins on Au Surfaces: Prototypical "Molecular Beacon" Biosensors. JACS 125: 4012 (2003).*
Dubertet et al., Single-mismatch detection using gold-quenched fluorescent oligonucleotides. Nature Biotechnology 19: 365 (2001).*
Evanko, D., Hybridization chain reaction. Nature Methods 1 (3): 186 (2004).*
Fan et al., Electrochemical interrogation of conformational changes as a reagentless method for the sequence-specific detection of DNA. PNAS 100 (16): 9134 (2003).*
Huang et al., Pyrene-Excimer Probes Based on the Hybridization Chain Reaction for the Detection of Nucleic Acids in Complex Biological Fluids. Angew. Chem. Int. Ed. 50: 401 (2011).*
Huang et al., Pyrene-Excimer Probes Based on the Hybridization Chain Reaction for the Detection of Nucleic Acids in Complex Biological Fluids. Supporting Information. Angew. Chem. Int. Ed. 50: 401 (2011).*
Huttanus et al., Enhanced Colorimetric Detection of DNAs via Catalytic Aggregation ogf Gold Nanoparticles. ACS Northwest Regional Meeting (Jun. 2012).*
Kennedy et al.,Locked nucleic acids for optimizing displacement probes for quantitative real-time PCR. Analytical Biochemistry 348 :294 (2006).*
Marras et al., Multiplex detection of single-nucleotide variations using molecular beacons. Genetic Analysis : Biomolecular Engineering 14: 151 (1999).*
Niu et al., Enzyme-enhanced fluorescence detection of DNA on etched optical fibers. Biosensors and Bioelectronics 24: 2943 (2009).*
Paleck, E., Surface-attached molecular beacons light the way for DNA sequencing. Trends in Biotechnology 22 (2) :55 (2004).*
Saiki et al., PNAS 86 :6230 (1989).*
The Stratagene Catalog [p. 39 (1988) ].*
Spiro et al.A Bead-Based Method for Multiplexed Identification and Quantitation of DNA Sequences Using Flow Cytometry. Applied and Environmental Microbiology 66 (10): 4258 (2000).*
Zuo et al., A novel sandwich assay with molecular beacon as report probe for nucleicacids detection on one-dimensional microfluidic beads array. Analytica Chimica Acta 587: 9 (2007).*
He Y. et al., "Visual Detection of Single-Nucleotide Polymorphism with Hairpin Oligonucleotide-Functionalized Gold Nanoparticles ", Anal. Chem., 2010, 82:7169-77.
Bakthavathsalam P. et al., "A direct detection of *Escherichia coli* genomic DNA using gold nanoprobes", J. Nanobiotech., 2012, 10:8.
Chang C.C. et al., "An amplified surface plasmon resonance "turn-on" sensor for mercury ion using gold nanoparticles", Biosensors and Bioelectronics, 2011, 30:235-40.
Luan Q. et al., "Hairpain DNA probe based surface plasmon resonance biosensor used for the activity assay of *E. coli* DNA ligase", Analyst, 2010, 135:414-18.
Fan H. et al., "A ne electrochemical method for DNA sequence detection with homogeneous hybridization based on host-guest recognition technology", Electrochem. Comm., 2010, 12:501-4.
Vo-Dinh T., "Nanobiosensing Using Plasmonic Nanoprobes", J. Selected Topics Quantum Electronics, 2008, 14 (1):198-205.
Tyagi S. et al., "Molecular Beacons: Probes that Fluoresce upon Hybridization", Nature Biotechnology, 1996, 14:303-308.
Renneberg D. and Leumann C.J., "Watson-Crick base-pairing properties of tricyclo-DNA", J. Am. Chem. Soc., 2002, 124:5993-6002.
Hurst S.J., "Maximizing DNA loading on a range of gold nanoparticle sizes", Anal. Chem., 2006, 78(24):8313-8.
European Communication pursuant to Article 94(3); dated Mar. 9, 2017.

* cited by examiner

US 9,909,166 B2

METHOD AND KIT FOR THE DETECTION OF NUCLEIC ACIDS

AREA OF THE INVENTION

The invention concerns a method for the determination of the concentration of a type of specific nucleic acids in a sample, wherein the sequences of the specific nucleic acids at least partially match a reference sequence, and/or for the determination of the degree of the match of the sequences of specific nucleic acids of a type in a sample with a reference sequence utilising a first probe, which possesses a first oligonucleotide on its surface and utilising a second oligonucleotide, which is partially complementary to the first oligonucleotide or to a first oligonucleotide adapter, which is partially complementary to the first oligonucleotide, and wherein the second oligonucleotide is partially complementary to the reference sequence. Additionally, the invention concerns providing a kit, which contains a first probe, which possesses a first oligonucleotide on its surface. Furthermore, the kit contains a second oligonucleotide, which is partially complementary to the first oligonucleotide or to a first oligonucleotide adapter, which is partially complementary to the first oligonucleotide.

BACKGROUND OF THE INVENTION

Methods for the detection of nucleic acids are known from the art. The patent specification U.S. Pat. No. 6,812,334 B1 discloses a method for the detection of nucleic acids. This method comprises the provision of nanoparticles, to which oligonucleotides are attached and of one or several kinds of connecting oligonucleotides. Each connecting oligonucleotide has two sections. The sequence of one section is complementary to the sequence of one of the sections of the nucleic acid and the sequence of the other section is complementary to the sequence of the oligonucleotides on the nanoparticles. The nanoparticle oligonucleotide conjugates, the connecting oligonucleotides and the nucleic acid are combined under hybridisation conditions and a detectable change occurs. The said patent specification also discloses a kit for carrying out the said method.

The European patent application EP 1 870 478 A1 discloses a biosensor, which consists of metal particles, which are fixed to the surface of a carrier. A probe molecule is fixed to these metal particles, wherein the probe molecule, in particular, may be a nucleic acid, which forms a hairpin structure. The probe molecule shows a fluorescence molecule. Before the reaction of the probe molecules with the target molecules, the distance between the metal particle and the fluorescence molecule is equal or less than 5 nm, such that the excitation energy of the fluorescence molecule is transferred to the metal particle. Thereby, the fluorescence quenched. The distance between fluorescence molecule and metal particle is greater after the reaction, such that the fluorescence molecule can fluoresce.

The patent application US 2010 0075335 A1 discloses a colorimetric method for the detection of specific nucleic acid sequences, inclusive of mutations and single nucleotide polymorphisms (SNPs) in nucleic acid sequences by aggregation of nanoparticles. In this method, identical nanoprobes with oligonucleotides are used, which are directly attached to gold nanoparticles, which appear red in a solution. The aggregation of these nanoprobes by an increase of ionic strength leads to a colour change from red to blue. The presence of the target DNA with a sequence, which is entirely complementary to the sequence of the nanoprobe prevents this aggregation and the solution remains red. The method is highly sensitive and makes it possible to differentiate sequences entirely complementary from sequences with one SNP. This patent application also discloses a kit for the application of the said method.

In the publication "Molecular beacons: probes that fluoresce upon hybridization" in Nature Biotechnology, 1996, volume 14, pages 303 to 308, S. Tyagi et al. report a novel principle for the production of probes, which are useful for the detection of specific nucleic acids in homogeneous solutions. Probes on the basis of this principle are single stranded nucleic acids molecules, which possess a stem loop structure. The loop part of the molecule is a probe sequence, which is complementary to a predetermined sequence of a target nucleic acid. The stem is formed by the hybridisation of two complementary arm sequences, which lie on either side of the probe sequence. The arm sequences are independent of the target sequence. A fluorescence donor group is added to one end of one arm and a non-fluorescing, quenching fluorescence acceptor group is added to the end of the other arm. The stem holds these two groups in great proximity, thereby the fluorescence of the fluorescence donor group is quenched by fluorescence resonance energy transfer. When the probe meets a target molecule, it forms a hybrid, which is longer and more stable than the hybrid formed by the arm sequences. In this way, the probe experiences a conformation change, which moves the arm sequences apart. As the fluorescence donor is not close to the fluorescence acceptor anymore, fluorescence is produced. These probes are described as molecular beacons.

Q. Luan, et al. present an *E. coli* DNA ligase biosensor in their publication "Hairpin DNA probe based surface plasmon resonance biosensor used for the activity assay of *E. coli* DNA ligase" in Analyst, 2010, volume 135, pages 414 to 418. In this sensor, a hairpin DNA probe is fixed to a gold film and hybridised to two single stranded DNA segments and, in this way, forms a hybrid with a discontinuity. When *E. coli* DNA ligase is present, the discontinuity is ligated, which leads to a conformation change of the hairpin DNA from the stem loop structure to a stiff double helix. This conformation change results in a change in the surface plasmon resonance.

Y. He et al. in their publication "'Visual detection of single nucleotide polymorphism with hairpin oligonucleotide functionalised gold nanoparticles" in Analytical Chemistry, 2010, volume 82, pages 7169 to 77 describe a lateral flow strip biosensor, in which a hairpin oligonucleotide is conjugated on its 5'-end with a gold nanoparticle and on its 3'-end it is modified with biotin. The hairpin oligonucleotide on the nanoparticle surface holds the biotin groups close to this surface, which leads to the biotin becoming "inactive". In this publication, the SNP detection is based on the unique properties of a hairpin oligonucleotide for the molecular differentiation of entirely complementary DNA from DNA with a single base change and the resulting different number of "active" biotin groups on the surface of the gold nanoparticles. After the hybridisation reaction, the gold nanoparticles, which contain activated biotin, are caught in the test zone of the lateral flow strip biosensor provided with immobilised streptavidin. The accumulation of gold nanoparticles in the test zone leads to a characteristic red band, whereby SNPs can be detected visually.

PROBLEM ACCORDING TO THE INVENTION

The invention is based on the problem to provide a method and a kit, which allows for an improved concentration detection of nucleic acids in a sample and which enables an improved detection of the degree of the match of specific nucleic acids of a type in a sample with a reference sequence.

SOLUTION ACCORDING TO THE INVENTION

According to the invention, the solution of the problem posed is attained—, by a method with the features of claim 1. The method serves the detection of the concentration of a type of specific nucleic acids in a sample, wherein the sequences of the specific nucleic acids at least partially match a reference sequence, and/or the methods serves the detection of the degree of the match of the sequences of specific nucleic acids of a type in a sample with a reference sequence. The method provides a first probe, which possesses a first oligonucleotide on its surface. Furthermore, the method according to the invention provides a second oligonucleotide, which is partially complementary to the first oligonucleotide or to a first oligonucleotide adapter, which is partially complementary to the first oligonucleotide. The second oligonucleotide is partially complementary to the reference sequence. Additionally, the method comprises the combining of the first probe and the second oligonucleotide and—if applicable—the first oligonucleotide adapter with the sample. Finally, a specific nucleic acid contained in the sample to be examined can hybridise with the second oligonucleotide and the second oligonucleotide can thereby be activated.

The solution of the problem posed is achieved, furthermore, by a kit with the features of claim 14. The kit comprises a first probe, which possesses a first oligonucleotide on its surface. The kit additionally contains a second oligonucleotide, which is partially complementary to the first oligonucleotide or to a first oligonucleotide adapter, which is partially complementary to the first oligonucleotide, wherein the second oligonucleotide can be activated by the hybridisation with a nucleic acid.

According to the invention, the first oligonucleotide adapter is optional, it need not be present for performing the method. This means that in one alternative of the method according to the invention a first oligonucleotide adapter is present, in a further alternative of the method according to the invention, however, no first oligonucleotide adapter is present. If the first oligonucleotide adapter is present, then it is partially complementary to the first oligonucleotide and partially complementary to the second oligonucleotide. If the first oligonucleotide adapter is not present, then the second oligonucleotide is partially complementary to the first oligonucleotide. Accordingly, the kit according to the invention need not contain a first oligonucleotide adapter.

The reference sequence is the sequence of a fictitious nucleic acid. The specific nucleic acids of a type are defined by the reference sequence. In the method, no nucleic acid with a sequence equal to the reference sequence needs to be present as an actual component of the sample, the method or the kit.

The specific nucleic acids belong to a type. Different individual specific nucleic acids may belong to the type. Each of the individual specific nucleic acids of the type has a sequence, which at least partially matches the reference sequence. In other words, a nucleic acid with a sequence, which does not at least partially match the reference sequence, does not belong to the type of specific nucleic acids. The sequences of the individual specific nucleic acids of the type can depend on the reference sequence according to a rule, in particular, for example, only individual specific nucleic acids with the sequence of a length equal to that of the reference sequence and which differ from the reference sequence in not more than one position may belong to the type. Another type, for example, may contain exclusively specific nucleic acids with sequences differing from the reference sequence exclusively in a particular area. Alternatively or additionally to the determination of the concentration of the type of specific nucleic acids in the sample, the invention can be used to determine the degree of the match of the sequences of specific nucleic acids of the type in the sample with the reference sequence. In one preferred embodiment, the invention allows to simultaneously obtain data on the degree of the match of the sequences of specific nucleic acids of the type in the sample with the reference sequence as well as the concentration of the type of specific nucleic acids with one measurement reading. The type may contain, for example, exclusively specific nucleic acids with sequences matching the reference sequence, that is specific nucleic acids of the same length as the reference sequence and containing identical nucleotides at each and every position.

Carrying out the method according to the invention in order to examine a sample is termed a test. The components of the kit can be used in conjunction with the sample for carrying out the test. The test result can be the concentration of the type of specific nucleic acids in the sample and/or the degree of the match of the sequences of specific nucleic acids of the type in the sample with the reference sequence.

Hybridisation according to the present invention means the forming of a double strand from two single strands, which each consist of a nucleic acid and/or an oligonucleotide. In suitable reaction conditions, the hybridisation typically leads to the lowest energy state, which can be achieved by combining the two single strands. In other words, this means that under suitable conditions, the single strands bind to each other in such a way that concerning the sequences of the two single strands, the greatest possible complementarity is created. The double strand can differ from the single strands in its physical properties, for example, the double strand can be stiffer than the single strands.

Determining the concentration of a type of specific nucleic acids in a sample means that the method according to the invention can lead to a measurement reading, from which the concentration of specific nucleic acids in the sample can be deduced, wherein the specific nucleic acids all belong to a type. Here, the concentration is the ratio of the number of all specific nucleic acids of the type in the sample and the volume of the sample. The correct determination of the concentration can lead to the value zero, this is true in the case, in which no nucleic acid is present in the sample, in which no specific nucleic acid of the type is present or in which specific nucleic acids of the type are only present at a concentration below the detection threshold of the method. In this, the detection threshold is the lowest concentration of a compound, at which concentration the method can detect the presence of the compound. Determination of the concentration of a nucleic acid may also mean that the method merely provides information on whether the concentration of the type of specific nucleic acids in the sample reaches at least a threshold value or not. If this threshold value is equal to the detection threshold then the method serves the detection of the type of specific nucleic acids. In this, detection means the answer to the question of whether specific nucleic acids of the type—at least at the concentration of the detection threshold—are present in the sample or not.

If a nucleic acid A is partially complementary to a nucleic acid B, this means that the sequence of the nucleic acid A in one part is complementary to one part of the sequence of the nucleic acid B. The match of a nucleic acid A with a nucleic acid B means that the sequences of the nucleic acids A and B are of the same length and contain the same nucleotides in each and every position. Partial match of a nucleic acid A with a nucleic acid B means that the sequences of the nucleic acids A and B contain identical oligonucleotides at least in one but not in all positions.

The determination of the degree of the match of the sequences of specific nucleic acids of a type in the sample with the reference sequence means that the method according to the invention can lead to a measurement reading, from which it can be deduced to what extent the sequences of the specific nucleic acids of the type in the sample match the reference sequence. Admissible results are, for example, complete match, sequence mismatch at a single position and 98% match. Determination of the degree of the match can also mean that the method may only differentiate between few discrete cases, for example, the differentiation of the following four cases: (1) The sample contains a type of specific nucleic acids with perfect match with the reference sequence, (2) the sample contains a type of specific nucleic acids with a sequence mismatch in a single position as compared to the reference sequence, (3) the sample contains a type of specific nucleic acids with a sequence mismatch in several positions compared to the reference sequence, (4) the sample contains exclusively nucleic acids without any match with the reference sequence or the sample contains no nucleic acid.

In the context of the present invention, the term oligonucleotide comprises not only (deoxy)oligoribonucleotides, but also nucleotides that contain one or more nucleotide analogues with modifications on their backbone (for example methylphosphonates, phosphothioates or peptide nucleic acids [PNA], in particular on sugar of the backbone (for example 2'-O-alkyl derivatives, 3'- and/or 5'-aminoriboses, locked nucleic acids [LNA], hexitol nucleic acids, morpholinos, glycol nucleic acids [GNA], threose nucleic acid [TNA] or tricyclo-DNA; in this regard see the publication by D. Renneberg and C. J. Leumann entitled "Watson-Crick base pairing properties of Tricyclo-DNA", J. Am. Chem. Soc., 2002, volume 124, pages 5993 to 6002, the related content of which forms part of the present disclosure by way of reference) or contain base analogues, for example 7-deazapurine or universal bases such as nitroindole or modified natural bases such as N4-ethyl-cytosine. In one embodiment of the invention, the oligonucleotides are conjugates or chimaeras with non-nucleosidic analogues, for example, PNA. In one embodiment of the invention, the oligonucleotides contain, at one or more positions non-nucleosidic units such as spacers, for example, hexaethylene glycol or $C_n$-spacers, where n is between 3 and 6. To the extent that the oligonucleotides contain modifications, these are chosen in such a way that a hybridisation with natural DNA/RNA-analytes is also possible with the modification. Preferred modifications influence the melting behaviour, preferably the melting temperature, in particular in order to distinguish hybrids having different degrees of complementarity of their nucleotides (mismatch discrimination). Preferred modifications comprise LNA, 8-aza-7-deaza-purine, 5-propinyl-uracil, 5-propinyl-cytosin and/or abasic interruptions in the oligonucleotide. Further modifications according to the invention are, for example, modifications with biotin, thiol and fluorescence donor and acceptor molecules. The first and second oligonucleotides according to the invention have a preferred length of between 15 and 150 nucleotides, especially preferred is a length between 40 and 100 nucleotides.

Nucleotides according to the invention are the nucleotides of DNA and RNA as well as nucleotide analogues including possible modifications, of which the oligonucleotides consist.

The specific nucleic acids according to the invention are oligonucleotides without a limitation of their length, that is without limiting the number of their nucleotides. Particularly, the definition of specific nucleotides includes genomic DNA and PCR products from biological samples. Preferably, the specific nucleic acids are DNA or RNA single strands. The first oligonucleotide adapter according to the invention contains at least one oligonucleotide. The terms nucleic acid and oligonucleotide are employed synonymously hereafter.

If a specific nucleic acid is present in the probe, wherein the specific nucleic acid sufficiently matches the reference sequence, then the specific nucleic acid can hybridise to the second oligonucleotide. Through the hybridisation with the specific nucleic acid, the second oligonucleotide is activated. The activation of the second oligonucleotide means that the second oligonucleotide undergoes a change and this change leads to an alteration of the affinity of the second oligonucleotide to another oligonucleotide. By this alteration of the affinity, a measurable change may occur, from which the concentration of the type of specific nucleic acids and/or the degree of the match of the sequences of specific nucleic acids of the type with the reference sequence can be determined. Advantageously, a second oligonucleotide can be provided, in particular, which through the activation alters its affinity to the first oligonucleotide or to the first oligonucleotide adapter. In this way, preferably, by the activation of the second oligonucleotide, the first probe can be connected via the first oligonucleotide and—if applicable—via the first oligonucleotide adapter with the second oligonucleotide, such that a measurable change can be produced. A probe according to the invention is a particle or a substrate. Oligonucleotides can be fitted to the probe according to the invention.

Conventional tests, for example, according to U.S. Pat. No. 6,812,334 B1, which contain the first probe with the first oligonucleotide and the second oligonucleotide, are based on the principle that the first oligonucleotide must be connected to the second oligonucleotide via the specific nucleic acid contained in the sample in order to produce a measurable change. If, in a conventional test, a sample with a high concentration of specific nucleic acids is examined, this can produce the paradoxical effect that only a small part of the first oligonucleotides can hybridise with the second oligonucleotides via the specific nucleic acids. On account of the high concentration of specific nucleic acids, in this effect, a large part of the first oligonucleotides is occupied with specific nucleic acids, which are not linked to first oligonucleotides. As the portion of first and second oligonucleotides not occupied with specific nucleic acids is small at a high concentration of specific nucleic acids, the occupied first and second oligonucleotides cannot be linked to a sufficient degree to unoccupied second or first oligonucleotides, respectively. As the measurable change of the conventional test is based on the first oligonucleotide being linked to the second oligonucleotide via the specific nucleic acid and as this link is not produced to a sufficient degree, this leads to the measurable change not being produced to a sufficient degree. In this way, the concentration of the specific nucleic acid is underestimated by the conventional test. At very high concentrations of specific nucleic acids, an underestimation of the concentration through to a false negative test result can emerge. In other words, if the test result is negative, it is uncertain whether no specific nucleic acid or very many specific nucleic acids are present in the sample, which represents a considerable limitation of this test.

The method according to the invention and the kit according to the invention provide the advantage that in order to determine the concentration of the type of specific nucleic acids and the degree of the match of the sequences of nucleic acids of the type with the reference sequence, the specific nucleic acid does not need to hybridise with the first, but only with the second oligonucleotide, which is activated by the hybridisation. According to the invention one component of the test does not need to be connected to another component of the test via the specific nucleic acid, therefore underestimations of the concentration and false negative test results can be avoided in the method according to the invention even at high concentrations of the type of specific nucleic acids.

PREFERRED EMBODIMENTS ACCORDING TO THE INVENTION

Advantageous designs and further developments that can be employed individually or in combination are the subject matter of the dependent claims.

The activation undergone by the second oligonucleotide by the hybridisation with a specific nucleic acid can be a conformation change of the second oligonucleotide. The conformation change can consist in a change of the tertiary structure of the second oligonucleotide. The conformation change can, for example, lead to parts of the second oligonucleotide being exposed such that those parts become available for a hybridisation with a nucleic acid. The conformation change can, for example, also lead to parts of the second oligonucleotide being covered such that they are not available for a hybridisation anymore. Preferably, the conformation change leads to an increase in the affinity of the second oligonucleotide to the first oligonucleotide or the first oligonucleotide adapter. The activation, which is experienced by the second oligonucleotide, can consist in a change in its physical or chemical properties, for example, a change in the total or partial charge, the production of fluorescence or the quenching of a fluorescence previously present or the exposure of a chemically reactive group. A conformation change can also lead to the oligonucleotide achieving or losing catalytic activity, for example, in the sense of a ribozyme.

In one embodiment of the invention, the activation of the second oligonucleotide leads to the first probe to be able to bind via the first oligonucleotide and—indirectly via the first oligonucleotide adapter or directly—via the second oligonucleotide—indirectly via a second oligonucleotide adapter or directly—to a second probe. In the context of the present invention, indirect binding means that the binding takes place via an adapter; the direct binding, however, occurs without a detour via an adapter. Through the binding of the first probe to the second probe, a measurable change can be produced. The first as well as the second oligonucleotide adapter are optional. This means that in a preferred embodiment the first and/or the second oligonucleotide adapter are not present and are not part of the method or kit respectively. Preferably, neither the first nor the second oligonucleotide adapter are part of the method. In this, the activation of the second oligonucleotide enables the first probe to bind via the first oligonucleotide and the second oligonucleotide directly to the second probe. More preferably, the second probe is directly connected to the second oligonucleotide; before the activation of the second oligonucleotide, for example, the second oligonucleotide contains a thiol modification, via which the second probe is connected with the second oligonucleotide, wherein the second probe is implemented as a nanoparticle, for example a gold nanoparticle. In this way, the method requires only two independent components i.e., the first probe with the first oligonucleotide at its surface and the second probe with the second oligonucleotide at its surface.

In an alternative embodiment it is preferred that the activation of the second oligonucleotide enables the first probe to bind via the first oligonucleotide and—indirectly via the first oligonucleotide adapter (as far as the first oligonucleotide adapter is present) or directly—via the second oligonucleotide and the second oligonucleotide adapter to the second probe. In this embodiment, the second oligonucleotide is not connected to a probe before the activation of the second oligonucleotide. To adapt the invention in this alternative embodiment to different reference sequences, the first oligonucleotide and the second oligonucleotide adapter do not necessarily have to be changed, merely the second oligonucleotide needs to be modified. This can be carried out in a simple, fast and inexpensive manner if the second oligonucleotide consists of an unmodified DNA molecule. More preferably, already before the activation of the second oligonucleotide, the second probe is connected directly at its surface to at least a part of the second oligonucleotide adapter, such that, advantageously, only three components are necessary for the method: First probe with first oligonucleotide, second probe with second oligonucleotide adapter and second oligonucleotide.

The functional oligonucleotides according to the invention comprise the first and second oligonucleotide and the first and second oligonucleotide adapter. The second oligonucleotide adapter according to the invention contains at least one oligonucleotide.

The first and second probes according to the invention can be implemented as mobile or immobile probes. In a preferred embodiment of the method, the first and second probes according to the invention can be implemented as mobile particles, for example, latex particles, pearls, beads, or metal particles.

In a preferred embodiment of the invention, the first and/or the second probe contain a nanoparticle. The nanoparticles according to the invention are particles, which due to their size possess certain optical properties, in particular characteristic absorption or scattering spectra, which are not or not as clearly present in the volume material. The nanoparticles have a diameter of less than 500 nm, preferably less than 150 nm. More preferably, nanoparticles have a diameter between 5 and 100 nm. The nanoparticles can be globular, but non-globular shapes, for example, rod-shaped nanoparticles are also possible. In a preferred embodiment of the invention, the nanoparticle comprises at least a metal, preferably a noble metal, for example, gold or silver. In one embodiment the nanoparticle fully consists of the metal, in another embodiment the metal only forms one part of the nanoparticle, for example, its shell.

In another embodiment of the invention, the first and second probes can be implemented as immobile substrate, for example, in the shape of a test strip or a metal film, especially a gold film. If the first or second probe are immobile, the respective other, second or first probe is preferably mobile. The probes according to the invention can, for example, consist of nanoparticles which are fixed to a gold film.

In one embodiment of the invention, the measurable change arises through an alteration of the distances of the first and second probes to each other. In one preferred embodiment of the invention, numerous first oligonucleotides are attached to the surface of the first probes and numerous second oligonucleotides or second oligonucleotide adapters are affixed to the surface of the second probes, such that through the activation of the second oligonucleotide a connection of the first and second probes can form, which leads to a measurable change. In a more preferable embodiment, the first and second probes are implemented as nanoparticles and the activation of the second oligonucleotide leads to a connection of the nanoparticles, such that through an alteration of the mean distance of the nanoparticles to each other, a change of the plasmon resonance of the nanoparticles occurs, such that the absorbance spectrum, for example, can be spectrally shifted and/or broadened.

A measurable change according to the invention can be determined, for example, by measuring an optical property or an optical effect such as reflection, diffraction, absorbance, by measuring the fluorescence, plasmon resonance, the magnetic flux or the displacement of a mass, in a preferred embodiment, the measurable change is detectable without auxiliary means and can be perceived with the naked eye as a colour change of the sample or the test strip. In a particular embodiment of the invention, the measurable change can be determined by using a light source. Preferably, the measurable change is determined by a laser, hereafter termed query laser, in this way, for example, the absorbance can be determined especially precisely. The wavelength of the light source and in particular of the query laser is preferably in a range from the far infrared to the far ultraviolet (in a range from 100 nm to 30 µm wavelength), more preferably in a range from near infrared to near ultraviolet (in a range from 200 nm to 3 µm wavelength), more preferably in the range of the visible light (in a range from 400 nm to 800 nm wavelength).

In a preferred embodiment of the invention, one or more functional oligonucleotides are modified with a fluorescence donor and/or fluorescence acceptor. In an especially preferred embodiment, the second oligonucleotide is modified with a fluorescence donor and a fluorescence acceptor, such that the activation of the second oligonucleotide produces a fluorescence or quenches a fluorescence previously present.

In a preferred embodiment of the invention, one or several functional oligonucleotides contain a hairpin. Preferably, the second oligonucleotide contains a hairpin. A hairpin according to the invention is an oligonucleotide, which contains two arms, which lie on either side of a central segment. The two arms are at least partially complementary to each other. In an initial state, the arms hybridise with each other and form a stem. The central segment forms a loop between the arms, such that a stem loop structure arises, which resembles a hairpin. According to the invention, the loop segment of the hairpin is at least partially complementary to the reference sequence. If a specific nucleic acid with a sequence sufficiently matching the reference sequence hybridises with the loop segment of the hairpin in the second oligonucleotide, the stiffness of the loop segment is increased, the hairpin opens under suitable conditions and exposes both its arms. In this embodiment, the opening of the hairpin represents the activation of the second oligonucleotide, which leads to the conformation change of the second oligonucleotide. By using a hairpin, a second oligonucleotide, which can be activated, can be provided in an especially simple way. In a more preferable embodiment, the second oligonucleotide consists of a hairpin, one arm of which is connected to the second probe. The free arm of the hairpin is complementary to the first oligonucleotide on the first probe. By hybridising with the specific nucleic acid with a sequence sufficiently matching the reference sequence, the hairpin opens and one arm of the hairpin hybridises with the first oligonucleotide, such that the first probe is connected to the second probe. In this especially preferred embodiment, merely two different components, which can be produced cheaply by using standard methods, are required for the method. It is especially preferred that the first oligonucleotides match the second oligonucleotides and the first probes equal the second probes, such that only one kind of oligonucleotides conjugated probes need to be combined with the sample.

In an especially preferred embodiment of the invention, the first and/or the second probe possess several different nucleic acids on their surface. More preferably, the first and/or second probe show one kind of nucleic acids, which do not hybridise with functional oligonucleotides, but merely serve as spacers for the functional oligonucleotides on the probe surface. Such spacers are also termed filling sequences and in a preferred embodiment, consist of poly-A-oligonucleotides, which contain adenine as their only base, or of poly-T-oligonucleotides, which contain thymin as their only base. Filling sequences according to the invention are no functional oligonucleotides. More preferably, the filling sequences are shorter than the functional oligonucleotides. The use of the filling sequences offers the advantage that the functional oligonucleotides on the probe surface cannot interfere with each other. In the case that the probe is implemented as a nanoparticle, the covering of the nanoparticles with filling sequences can avoid an undesired aggregation of the nanoparticles on account of the electrostatic repulsion between DNA molecules. If a hairpin is affixed to the surface of the first and/or the second probe, an oligonucleotide shorter than the hairpin can be attached to the same probe, which oligonucleotide is at least partially complementary to the free arm of the hairpin. In this alternative embodiment, the free arm of the hairpin can hybridise to the shorter oligonucleotide. This makes it possible, to vary the arm of the hairpin, which is attached to the probe surface independently of the free arm, which can be an advantage when designing a complex test, in particular.

In a further preferred embodiment of the invention, two or more independent methods are carried out in the sample simultaneously and the concentration of two or more different types of nucleic acids are determined by a measurement, which is read out at different temperatures. In a preferred embodiment, the nucleic acids of the type A hybridise at a temperature below the melting temperature A with the functional oligonucleotide A and thereby activate it; the nucleic acids of the type B hybridise at a temperature below the melting temperature B with the functional oligonucleotide B and thereby activate it. The melting temperatures are chosen such that at a first temperature, the nucleic acids of the type A hybridise with an oligonucleotide A. This first temperature, however, is too high for a hybridisation of a nucleic acid of the type B with the oligonucleotide B to occur. The measurement reading, which is determined at the first temperature, allows the deduction of the concentration of the nucleic acids of the type A, however, no deduction concerning the concentration of the nucleic acids of the type B is possible. At a second temperature, the nucleic acids of the type A hybridise with the oligonucleotide A and the nucleic acids of the type B hybridise with the oligonucleotide B. The measurement reading determined at the second temperature depends on the concentration of the nucleic acids of the type A and the nucleic acids of the type B. The two measurement readings, which are determined at the first and the second temperature allow the inference of the concentration of the nucleic acids of the type A and the concentration of the nucleic acids of the type B, when analysed appropriately. Accordingly, n different types of nucleic acids can be examined in a sample by n independent tests, when the melting temperatures of the individual tests are chosen such that when measuring at n different temperatures, an inference of the concentrations of each individual of the n types of nucleic acids is possible. In this, n is limited by the restricted temperature range, in which an aqueous solution can be examined and by a minimal, required distance of the n different temperatures to each other. More preferably, in this embodiment of the invention, the first and/or the second probes are implemented as nanoparticles and the change of the temperature can be attained by exciting the nanoparticles with an electromagnetic radiation source. In this, the excitation of the nanoparticles preferably heats the immediate surroundings of the nanoparticles more strongly than the wider surroundings. In this embodiment, a temperature change can be created especially rapidly such that the concentration of several different types of nucleic acids in the sample can be determined in a short period of time. The same method of temperature change is applicable to detect the degree of the match of several types of nucleic acids present in the probe at the same time and each of their query nucleic acids.

In a particularly preferred embodiment, which allows the execution of two or more independent methods in a sample, the oligonucleotides are implemented as hairpins. If specific nucleic acids are present, the hairpins do not open at a first, low temperature, as the arm sequences of the hairpins are bonded tightly to each other at the first temperature and the specific nucleic acids, therefore, cannot bind to the hairpins. At a higher, second temperature, the specific nucleic acids can bind to the hairpins and can open these as the connection of the arm sequences is looser at the second temperature. Thereby, the probes according to the invention can be connected via the hairpins. At a third temperature, which is higher than the second temperature, the specific nucleic acid dehybridises from the hairpins and/or two or more oligonucleotides involved in the connection of the first and second probes dehybridise from each other. Thus, the probes are separated again at the third temperature. In order to carry out two or more independent methods in one sample, first hairpins can be used for the detection of the specific nucleic acid and second hairpins can be used for the detection of an additional nucleic acid. The sequences of the hairpins are chosen such that a second temperature of the first hairpin is at the same time a first temperature of the second hairpin. At the same time, a second temperature of the second hairpin is a third temperature of the first hairpin and its oligonucleotides. In other words, it is possible at a lower temperature for specific nucleic acids to open the first hairpin, however, the lower temperature is too low for the additional nucleic acid to open the second hairpin. At a higher temperature, the additional nucleic acids can open the second hairpin. In this, the higher temperature is such that the specific nucleic acid dehybridises from the first hairpin and/or that the probes, which can be connected via the first hairpin, can be separated by dehybridisation from at least two oligonucleotides connecting these probes. In this way, advantageously, the concentrations of the specific and additional nucleic acids can be determined through a measurement at two different temperatures and with little effort. When arranged accordingly, further hairpins can be used to determine the concentrations of further nucleic acids at further temperatures in the same probe.

In a preferred embodiment according to the invention, the first and/or second oligonucleotide adapter consists of several oligonucleotides, which are partially complementary to each other. The oligonucleotides partially complementary to each other can hybridise with each other and can, in this way, be connected to yield an oligonucleotide adapter. The first and second oligonucleotide adapters, which consist of several oligonucleotides partially complementary to each other, are termed multipart oligonucleotide adapters hereafter. If parts of the test are modified, for example, in order to adapt the test to different reference sequences, it can be necessary that the first and/or the second oligonucleotide adapter need to be adapted to altered first and/or second oligonucleotide. In this case, when using a multipart oligonucleotide adapter, it is achievable that of the oligonucleotides, from which the multipart oligonucleotide adapter is made up, only a single one needs to be varied in order to achieve the desired adaptation of the oligonucleotide adapter. That part of the oligonucleotide adapter, which is not altered, can be used in several versions of the test, whereby production costs can be saved.

In another preferred embodiment of the invention, in addition to the second oligonucleotide at least one further functional oligonucleotide is activated by the hybridisation with an oligonucleotide or a nucleic acid. More preferably, the method provides two or several measurement readings, by which the concentration of the type of the specific nucleic acids and one or several further types of nucleic acids present or their degree of match with the reference sequence and further query nucleic acid sequences can be inferred. In a further especially preferred embodiment, an activatable functional oligonucleotide can activate another or a part of another activatable functional oligonucleotide or several other activatable functional oligonucleotides. In this way, a signal cascade can be produced in the test to lead to an amplification of the entry signals such that a higher sensitivity of the method can be provided.

In another embodiment of the invention, the further functional oligonucleotide can be activated by a nucleic acid B and the measurable change is produced in a logical AND-function if and only if the nucleic acid A as well as the nucleic acid B are present in the sample in a sufficient concentration. In this case, the specific nucleic acid is identical with nucleic acid A. In a medical test, for example, a positive result only occurs when the concentration of nucleic acid A as well as nucleic B are above a threshold value. The logic AND-function can be implemented if in addition to an activatable second oligonucleotide by nucleic acid A, for example, the first oligonucleotide is activatable by nucleic acid B and a measurable change occurs if and only if the first as well as the second oligonucleotide are activated.

In a further embodiment of the invention, binary entry values of the nucleic acids in the sample are logically linked, such that a binary output value is produced according to the logic link. The binary entry value of the nucleic acid in the sample is logic 1, if the concentration of the nucleic acid in the sample is above a threshold value, otherwise the binary entry value is logic 0. In this embodiment, a measurable change can occur, which can be verified by a measurement reading. If the measurement reading is above a threshold value then the output value is logic 1, otherwise the output value is logic 0. For example, a test can be designed such that the test result is positive if and only if the binary output value is logic 1. Nucleic acids present in the sample are termed nucleic acid A, nucleic acid B and nucleic acid C hereafter. In this, nucleic acid A corresponds to the specific nucleic acid. The binary entry value of the nucleic acid is termed A, the entry value of nucleic acid B is termed B and the entry value of nucleic acid C is termed C. A is logic 1 if the concentration of the nucleic acid is above a threshold value, otherwise A is logic 0. More preferably, the method allows the provision of tests with arbitrary logic functions of the binary entry values with Boolean operators such, for example, NOT, OR, AND, NAND, NOR and XOR. Especially in medical application, it can be of advantage, to obtain a positive test result (corresponding to an output value of logic 1) exclusively when nucleic acid A and/or nucleic acid B (A OR B) are present. In certain medical questions it can be of an advantage to only obtain a positive test result according to a complex linking of markers. For example, the invention enables the implementation of a complex logic function such as (A AND B) AND NOT C, such that when a nucleic acid A and nucleic acid B is present, a present nucleic acid C prevents a positive test result. The NOT function can be realised, for example, by a hairpin, which is present in excess and which—after it is opened— occupies a large part of the functional oligonucleotides attached to the probes, such that a connection of first and second probes is prevented. The (A OR B) function can, for example, be produced by the nucleic acid A being able to activate the second oligonucleotide and the nucleic acid B being able to activate a third oligonucleotide, wherein the third oligonucleotide only differs from the second oligonucleotide in that the part complementary to the nucleic acid A is replaced by a part complementary to the nucleic acid B. The activated third oligonucleotide can, in this way, lead to an essentially identical measurable change as the activated second oligonucleotide, independently of the second oligonucleotide. The methods of logical linking are described in an exemplary fashion with the three nucleic acids A, B and C, however, the methods are not limited to only three different nucleic acids, rather in a suitable implementation an unlimited number of different nucleic acids in a sample can be examined simultaneously, in principle. The methods of logical linking described can also be carried out instead of the nucleic acids A, B and C, which each contain a sequence exactly defined, with different types (for example type A, type B and type C) of nucleic acids, wherein a type of nucleic acids, for example, only activates one functional oligonucleotide.

It is possible, to read out binary entry as well as output values in a test, for example, if the activatable functional oligonucleotides are provided with a fluorescence donor and acceptor, wherein the fluorescence in the deactivated state of the oligonucleotide is quenched by the small distance of the fluorescence donor to the fluorescence acceptor. Through the activation, the distance between fluorescence donor and acceptor increases and fluorescence occurs. In other words, the activatable functional oligonucleotides, in this case, are implemented as molecular beacons (described in S. Tyagi et aL, supra). By reading out the fluorescence of the functional oligonucleotides, the activation states of the oligonucleotides and, thereby, the entry values can be read out. Through the activation, in addition to the change in fluorescence, the activatable functional oligonucleotides alter their affinity to each other and/or to further oligonucleotides in such way that the binary output value is produced according to the chosen logical link of the entry values. In this fashion, advantageously, entry as well as output values can be read out in one test.

In another preferred embodiment of the invention, the measurable change is determined before and after excitation of the first and/or second probes by a light source. The light source is preferably a heating laser. Before the excitation the specific nucleic acid hybridises with the second oligonucleotide and activates the second oligonucleotide, thereby, the first probes are connected to the second probes via a chain of oligonucleotides. Components of this chain are, in any case, the first and second oligonucleotide, depending on the implementation also the first and/or second oligonucleotide adapter. By connecting the first with the second probes, a measurable change occurs. By the excitation of the probes with the light source, the specific nucleic acids dehybridise from the second oligonucleotides and/or at least one part of the chain dehybridises from another part, such that the first and the second probes are separated and no measurable change can be measured anymore. It is especially preferred if the first and second probes are nanoparticles and the measurable change is a change of the absorbance spectrum on account of an alteration of the plasmon resonance of the nanoparticles, which can be read out with a query laser. Advantageously, by measuring after the excitation, an internal negative control can be created.

The excitation of the nanoparticles preferably occurs in an alternating field, especially preferably through an electromagnetic radiation source. The electromagnetic radiation source is preferably a light source, more preferably it is a laser, termed heating laser hereafter, a light emitting diode (LED) or a flash light. The light source can emit the light continuously or pulsed. Monochrome as well as polychrome, in particular, white light sources can be used. The light of the light source according to the present invention is in the range from far infrared to far ultraviolet (in a range of 100 nm to 30 µm wavelength), more preferably in the range from near infrared to near ultraviolet (in a range from 200 nm to 3 µm wavelength), more preferably in the visible range (in a range from 400 nm to 800 nm wavelength). It is also possible to excite the nanoparticles according to the invention with radio frequency, for example, with a magnetic radio frequency field.

If nanoparticles are used as probes, they are preferably excited in such way that the immediate surroundings of the nanoparticles are heated by the excitation of the nanoparticles more strongly than the further surroundings of the nanoparticles. In this, the immediate surroundings of the nanoparticles are preferably a spherical volume, which has the 100-fold diameter of the nanoparticle, which is situated in its centre, more preferably the volume hast the 10-fold diameter, more preferably the 4-fold diameter and most preferably less than the 2-fold diameter. By the exclusive heating of the immediate surroundings of the nanoparticle, the heating can be carried out more rapidly and with a lower energy expenditure.

Preferably, an exclusively local heating of the surroundings of the nanoparticles takes place by the excitation of the nanoparticles. The heating is termed local if the duration of the excitation t is smaller than t1. In this, $t1=(s1*|x|)^2/D$, wherein $|x|$ is the mean nanoparticle distance and D is the thermal diffusivity of the liquid in the sample, in aqueous solutions this is typically $D=10^{-7}$ m$^2$/s. The scaling factor s1 is preferably s1=100, preferably s1=30, preferably s1=10, preferably s1=7, preferably s1=3 and most preferably s1=1, preferably s1=0.7, preferably s1=0.3. In this especially preferred embodiment in which a local heating takes places, the teachings of Keblinski et al. (J. Appl. Phys., 100, 054505, 2006) and from EP 2162549 are taken into account, the relevant portions of which are part of the present disclosure by way of reference. A local heating can, advantageously, take place rapidly and at a low energy expenditure.

Advantageously the invention makes it possible to provide a method and a kit, which enable an improved detection of the concentration of a type of specific nucleic acids in a sample and which enables the improved determination of the degree of the match of the sequences of specific nucleic acids of a type in a sample with a reference sequence.

BRIEF DESCRIPTION OF THE FIGURES

The invention is illustrated hereafter using drawings and experimental results in several embodiments and in more details.

It is shown in.

DETAILED DESCRIPTION OF THE INVENTION ACCORDING TO SEVERAL EMBODIMENTS

Figure 1:
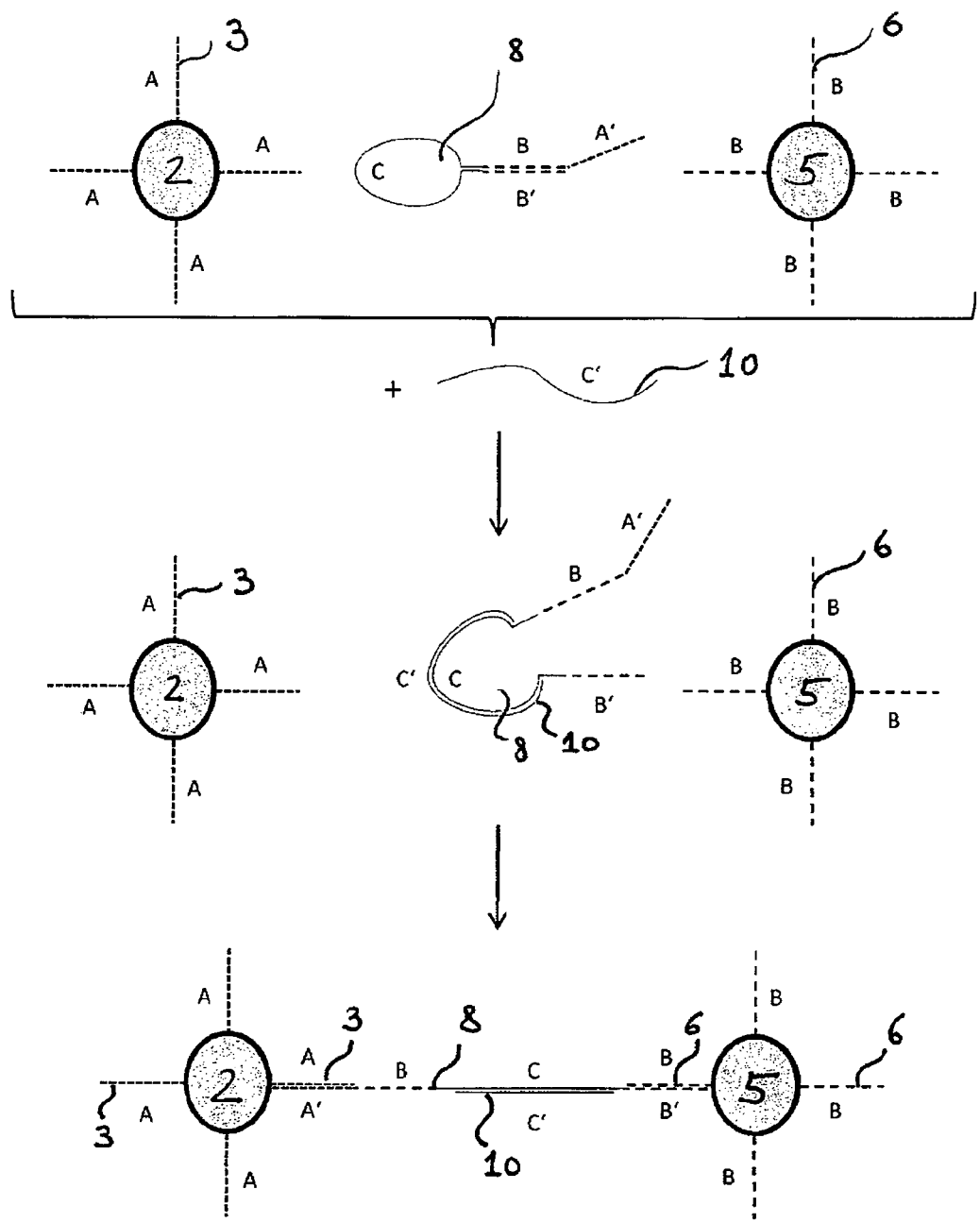
FIG. 1 a schematic representation of the method according to the invention with two nanoparticles and a free second oligonucleotide as hairpin and the specific nucleic acid.

FIG. 1 shows a first probe 1, which is implemented as a first nanoparticle 2 and which shows a first oligonucleotide 3 with the sequence A at its surface. Furthermore, a second probe 4 is shown, which is implemented as a second nanoparticle 5 and which shows a second oligonucleotide adapter 6 at its surface, which has the sequence B. A second oligonucleotide 7 is implemented as a hairpin 8, which has the sequence C in its loop segment and the arm sequences of which are B and B'. A nucleotide sequence A' is attached to the arm with the sequence B. In a sample 9, a specific nucleic acid with the sequence C' is present, which hybridises with the loop segment of the hairpin, whereby the hairpin 8 opens. By opening the hairpin 8, the sequence B' at the hairpin 8 becomes free and the first nanoparticle 2 can hybridise with the sequence A' of the hairpin 8 via the sequence A of the first oligonucleotide 3 and the sequence B of the second oligonucleotide adapter 6 on the surface of the second nanoparticle 5 can hybridise with the sequence B' of the hairpin 8. In this way, the first nanoparticle 2 is connected with the second nanoparticle 5 via the hairpin 8. This can, for example, be detected as a redshift and broadening of the plasmon resonance in the absorbance spectrum.

Figure 2A:
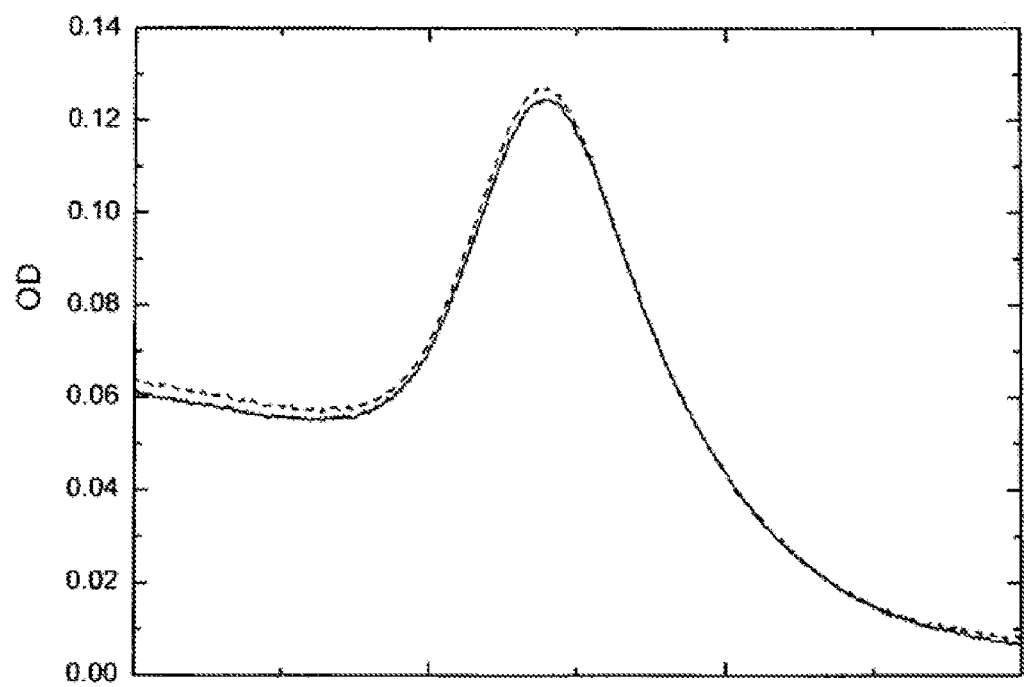
FIG. 2*a* two absorbance spectra of a mixture of first nanoparticles, which are functionalised with the sequence ID1a and of second nanoparticles, which are functionalised with the sequence ID1b, in a diagram, in which the optical density (OD) is plotted against the wavelength λ in nanometers (nm)

FIG. 2a shows absorbance spectra from an experiment. In this experiment, the first probes 1 and the second probes 4 are carried out as nanoparticles 11 made of gold with a diameter of 60 nm. The first probes are present in a solution at concentration of 5 pM, wherein the first probes 1 are functionalised on their surface with first oligonucleotides 3, which have the sequence ID1a. Furthermore, the solution contains second probes 4 at a concentration of 5 pM, which are functionalised on their surface with second oligonucleotide adapters 6, which have the sequence ID1 b. In the experiment in FIG. 2a, no activatable, second oligonucleotide 7 is present. In the absence of a specific nucleic acid 10 and of a second oligonucleotide 7, the first probes 1 cannot be connected to the second probes 4, which results in a narrow plasmon resonance as a typical sign for non-connected particles (continuous line). Even if a specific nucleic acid 10 with the sequence ID5 is added, no change in the absorbance spectra can be seen as, in this case as well the probes cannot be connected to each other as no second oligonucleotide 7 is present (dashed line).

Figure 2B:
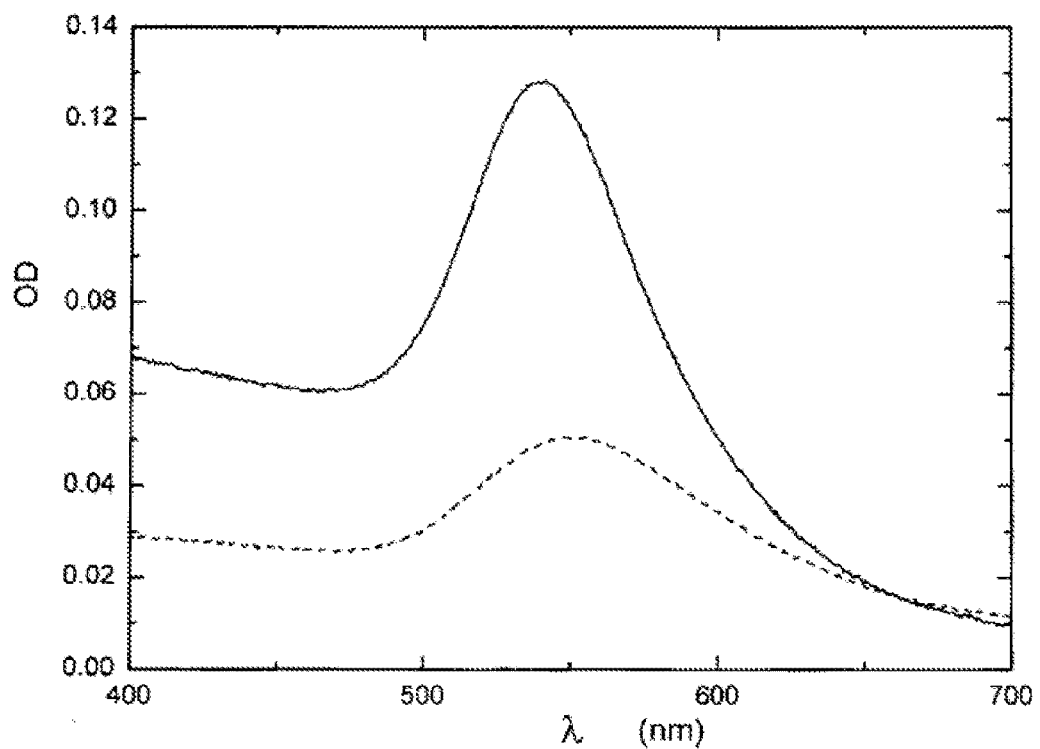
FIG. 2*b* two absorbance spectra of a mixture of first nanoparticles, which are functionalised with the sequence ID1a and of second nanoparticles, which are functionalised with the sequence ID1b in the presence of a second oligonucleotide with the sequence ID2 in a diagram, in which the optical density (OD) is plotted against the wavelength λ in nanometers (nm)

The diagram in FIG. 2b shows absorbance spectra of the first probes 1 and the second probes 4 from FIG. 2a at a concentration of 5 pM each, wherein additionally, a second oligonucleotide 7 with the sequence 102 is present at a concentration 500 pM. In the absence of a specific nucleic acid 10, the absorbance spectrum shows a narrow plasmon resonance after 24 hours (continuous line) as a typical sign for non-connected particles. Approximately 24 hours after adding 2 nM specific nucleic acid 10 with the sequence ID5, a clear change in the absorbance spectrum can be seen as a result of the connection of the particles (dashed line). This shows that the second oligonucleotide 7 does not connect the nanoparticle in its inactivated state as the hairpin 8 of the second oligonucleotide 7 is closed. However, if the specific nucleic acid 10 and the second oligonucleotide 7 are present in the solution, the specific nucleic acid 10 activates the second oligonucleotide 7, the hairpin 8 opens and the first probe 1 is connected to the second probe 4 via the second oligonucleotide 7, such that the absorbance spectrum changes. In this experiment, 20 mM phosphate buffer, 500 mM NaCl and 15% formamide are present in the solution. The nanoparticles were functionalised according to the method of Hurst et al. (S. J. Hurst et al., Analytical Chemistry, volume 78, pages 8313 to 8318, 2006), the absorbance spectra were recorded in a quartz cuvette with a 3 mm optical path and a Varian Cary 50 spectrometer.

Figure 3:
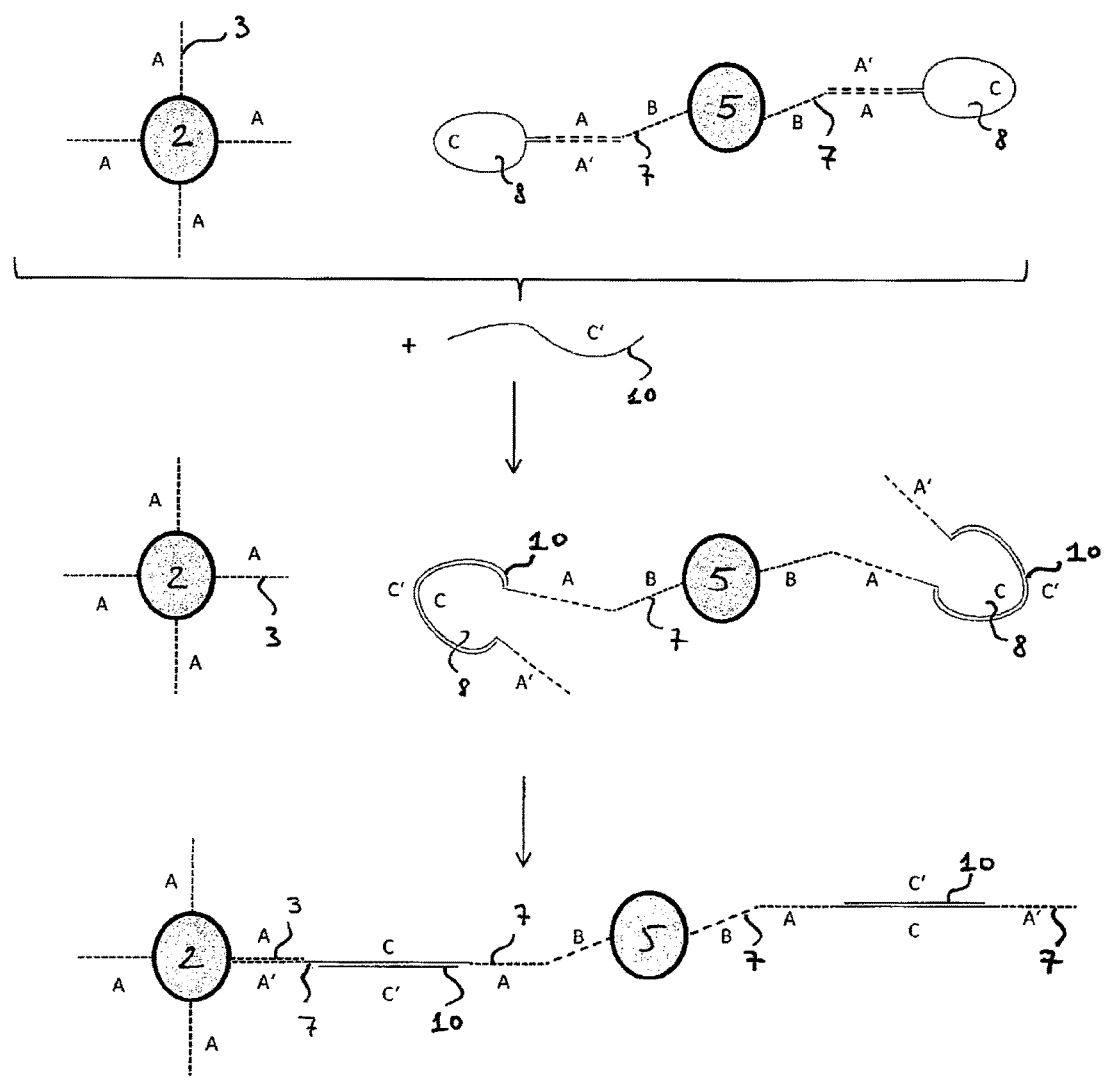
FIG. 3 in a schematic representation of the method according to the invention with the specific nucleic acid in the sample, a first and a second nanoparticle and the second oligonucleotide, which is implemented as a hairpin and which is attached to the surface of the second nanoparticle.

FIG. 3 shows a first probe 1, which is implemented as a first nanoparticle 2, which shows first oligonucleotides 3 with the sequence A at its surface and a second probe 4, which is implemented as a second nanoparticle 5, which shows a second oligonucleotide 7 at its surface, which is implemented as a hairpin 8. The hairpin 8 contains in its loop segment the sequence C and its arm sequences A and A', wherein a nucleotide sequence B is attached to the arm sequence A, which nucleotide sequence B connects the hairpin 8 with the surface of the second nanoparticle 5. A specific nucleic acid 10 with the sequence C' is present in a solution, which sequence C' binds to the loop segment of the hairpin 8, whereby the hairpin 8 opens. By opening the hairpin 8, the arm sequence A' becomes free, which hybridises with the first oligonucleotide 3 on the surface of the first nanoparticle 2. Thereby, the first nanoparticle 2 is connected to the second nanoparticle 5 via the first oligonucleotide 3 and the second oligonucleotide 7. This can be detected, for example, as redshift and broadening of the plasmon resonance in the absorbance spectrum.

Figure 4:
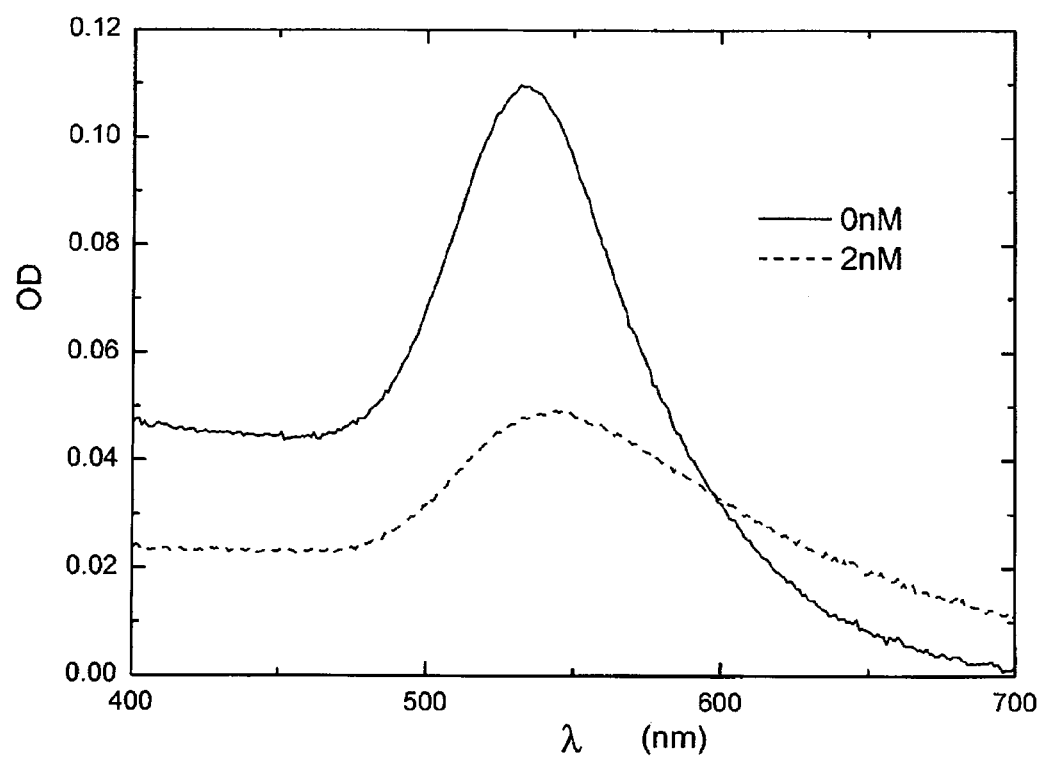
FIG. 4 two absorbance spectra of a mixture of first nanoparticles, which are functionalised with the sequence ID3 and of second nanoparticles, which are functionalised with the sequences ID3 and ID4 in a diagram, in which the optical density (OD) is plotted against the wavelength λ in nanometers (nm)

The diagram in FIG. 4 shows absorbance spectra from an experiment, in which first probes 1 and second probes 4 are implemented as nanoparticles 11 made of gold with a diameter of 60 nm. Attached to the surface of the first probe 1 are first oligonucleotides 3 with the sequence ID3 and attached to the surface of the second probe 4 are one part second oligonucleotides with the sequence ID4 and four parts oligonucleotides with the sequence ID3 as filling sequence. The concentration of the first probes 1 is 5 pM and the concentration of the second probes 4 is 5 pM. In the absence of the specific nucleic acid 10, the absorbance spectrum shows a narrow plasmon resonance after approximately 24 hours (continuous line). Approximately 24 hours after the edition of the specific nucleic acid 10 with the sequence ID5 at a concentration of 2 nM a clear redshift and broadening of the plasmon resonance in the absorbance spectrum can be seen as a result of the connection of the probes (dashed line). In this experiment, the concentration of the buffer is 20 mM phosphate buffer, 500 mM NaCl, 50% formamide. The nanoparticles were functionalised according to the method of Hurst et al., supra. The extinction spectra were recorded in a quartz cuvette with a 3 mm optical path and a Varian Cary 50 spectrometer.

Figure 5:
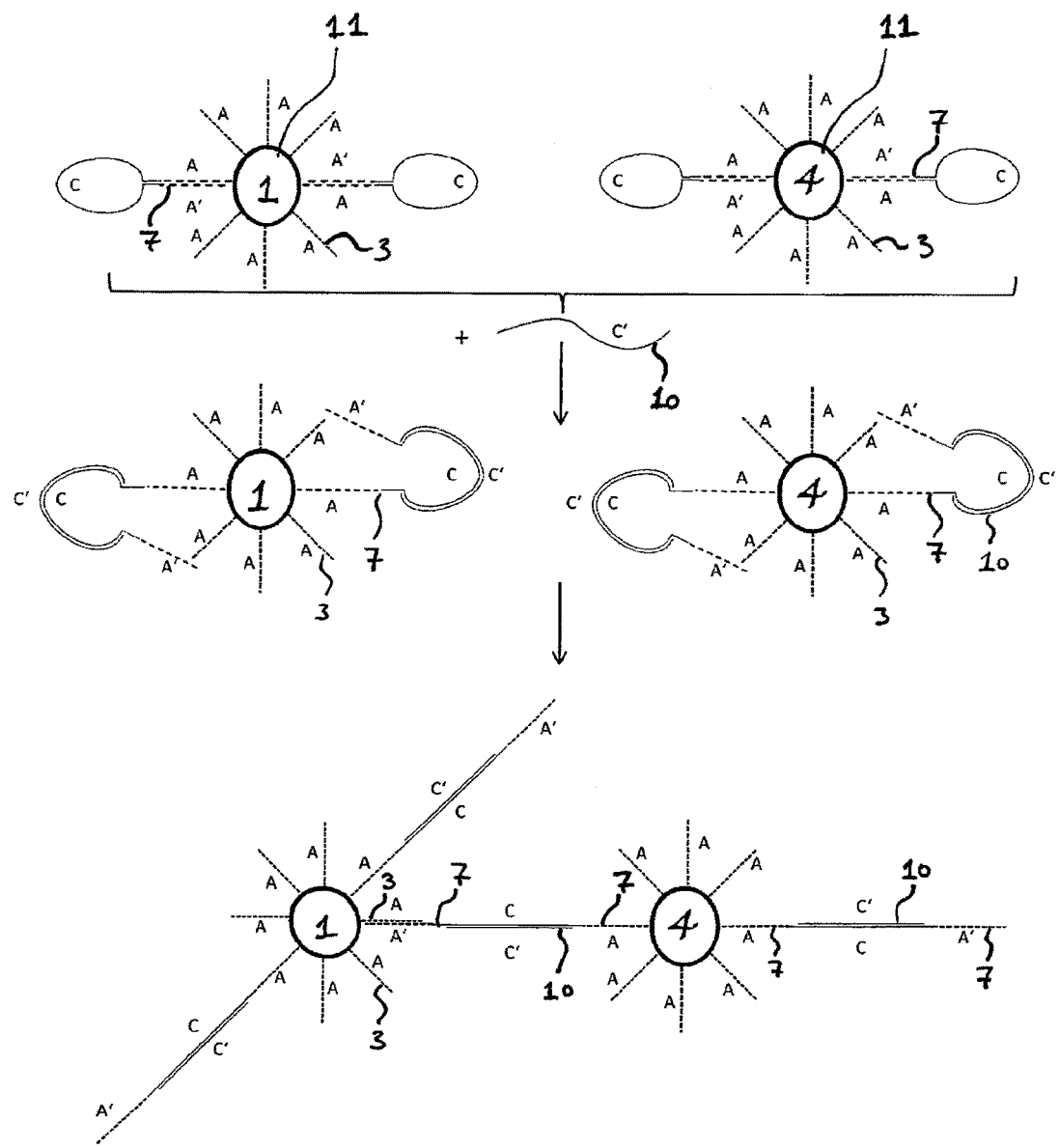
FIG. 5 in a schematic representation of the method according to the invention with a specific nucleic acid with two identical probes implemented as nanoparticles, which each contain first as well as second oligonucleotides on their surface, wherein the second oligonucleotide is carried out as a hairpin.

In FIG. 5, first probes 1 and second probes 4 are present in a solution, wherein the first probes 1 are identical with the second probes 4 and wherein they are implemented as nanoparticles 11, wherein the nanoparticles 11 show first oligonucleotides 3 at their surface, which have the sequence A and wherein the nanoparticles 11 also show second oligonucleotides 7, which consist of the partial sequences A, C and A'. The sequence C is complementary to the sequence C' of the specific nucleic acid 10. The sequence A' is complementary to the sequence A. Without the specific nucleic acid 10 with the sequence C' to be detected, the second oligonucleotide 7 forms a hairpin structure by the hybridisation of the partial segment A with A'. Thereby, the partial segment A' is blocked and cannot hybridise to another nanoparticle 11. In the presence of the specific nucleic acid 10 to be detected with the sequence C', the specific nucleic acid 10 hybridises to the partial segment C on the second oligonucleotide 7, which, as a result, dissolves its hairpin structure. Now, the partial segment A' is free and can hybridise to the first oligonucleotide 3 with the sequence A on another nanoparticle 11, whereby two or more nanoparticles 11 are connected. This can, for example, be detected as redshift and broadening of the plasmon resonance in the absorbance spectrum.

Figure 6:
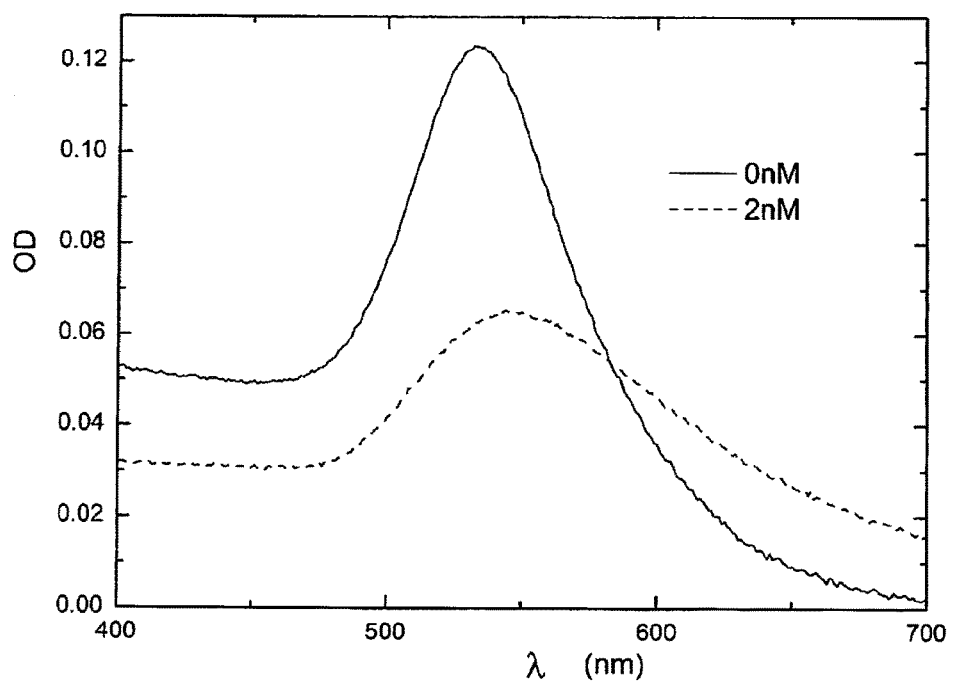
FIG. 6 two absorbance spectra of a mixture of gold nanoparticles, which are each functionalised with the sequence ID3 as well as the sequence ID4, in a diagram, in which the optical density (OD) is plotted against the wavelength λ in nanometers (nm)

FIG. 6 shows absorbance spectra of first probes 1 and second probes 4, which are identical and are implemented as nanoparticles 11 made of gold with a diameter of 60 nm. On the surface of the nanoparticles 11, two different oligonucleotides are attached: Four parts oligonucleotides with the sequence ID3 as filling sequence and one part first oligonucleotides 3 and second oligonucleotides 7, both of which have the sequence ID4. The concentration of the nanoparticles 11 made of gold is 10 pM. In the absence of the specific nucleic acid, the absorbance spectrum shows a narrow plasmon resonance (continuous line) after 24 hours. Approximately 24 hours after the addition of 2 nM of the specific nucleic acid 10 with the sequence ID5, a clear redshift and broadening of the plasmon resonance in the absorbance spectrum can be observed as a consequence of the connection of the particles (dashed line). In this experiment, 20 mM phosphate buffer, 500 mM NaCl and 50% formamide were used. The nanoparticles 11 were functionalised according to the method of Hurst et al., supra. The absorbance spectra were recorded in a quartz cuvette with an optical path of 3 mm in a Varian Cary 50 spectrometer.

Figure 7:
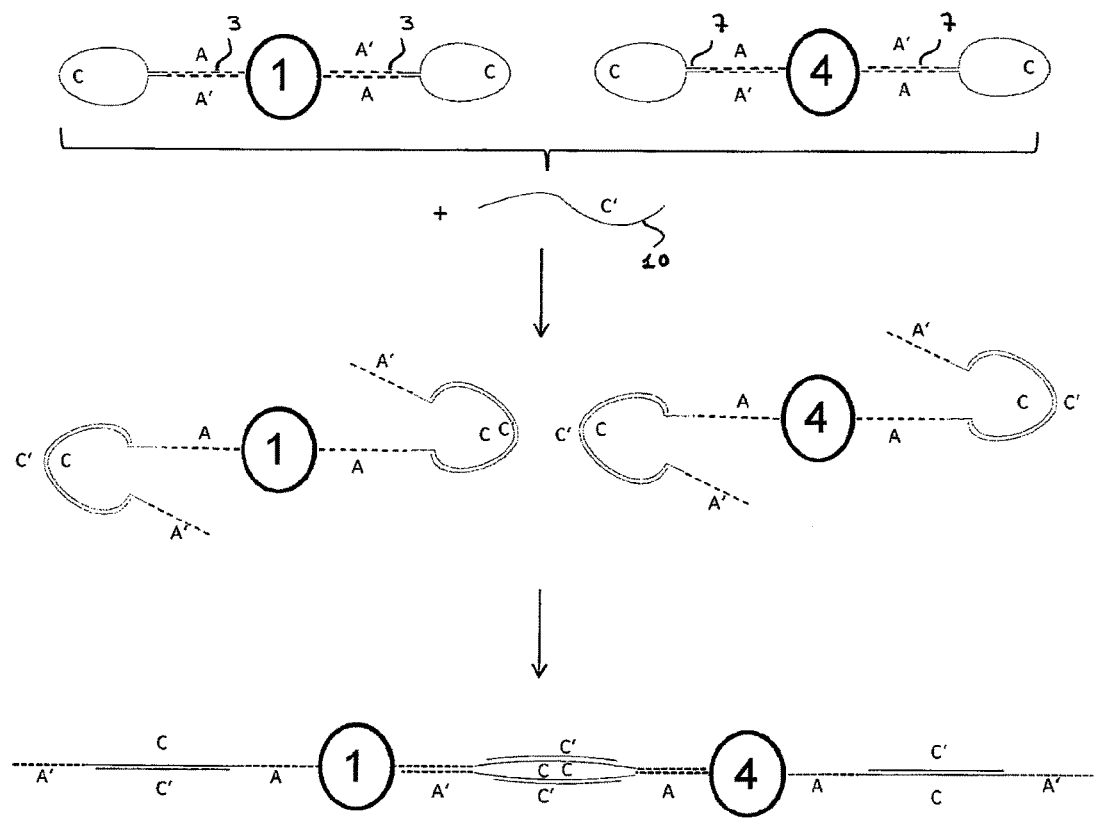
FIG. 7 in a schematic representation of the method according to the invention with a specific nucleic acid, with two identical probes implemented as nanoparticles, which show only one kind of oligonucleotides on their surface.

FIG. 7 shows first probes 1 and second probes 4, which are both implemented as nanoparticles 11 with first oligonucleotides 3 and second oligonucleotides 7, wherein the first oligonucleotides 3 and the second oligonucleotides 7 are identical and the first probes 1 and the second probes 4 are identical. The first oligonucleotides 3 and second oligonucleotides 7 consist of the partial sequences A, C and A'. The partial sequence C is complementary to the specific nucleic acid 10 with the sequence C' and the partial sequence A' is complementary to the partial sequence A. In the absence of the specific nucleic acid 10 with the sequence C', which is to be detected, the first oligonucleotide 3 and the second oligonucleotide 7 form a hairpin structure by the hybridisation of the partial segment A with A'. Thereby, the partial segment A' is blocked and cannot hybridise onto other nanoparticles 11. In the presence of the specific nucleic acid 10 with the sequence C', which is to be detected, the specific nucleic acid hybridises to the partial segment C of the first oligonucleotide 3 or the second oligonucleotide 7, which as a result of this dissolves its hairpin structure. Now, the partial segments A and A' are free and can hybridise to the partial segments A' and A on another nanoparticle 11, whereby two or more nanoparticles 11 are connected. This can be detected, for example, as a redshift and broadening of the plasmon resonance in the absorbance spectrum.

Figure 8:
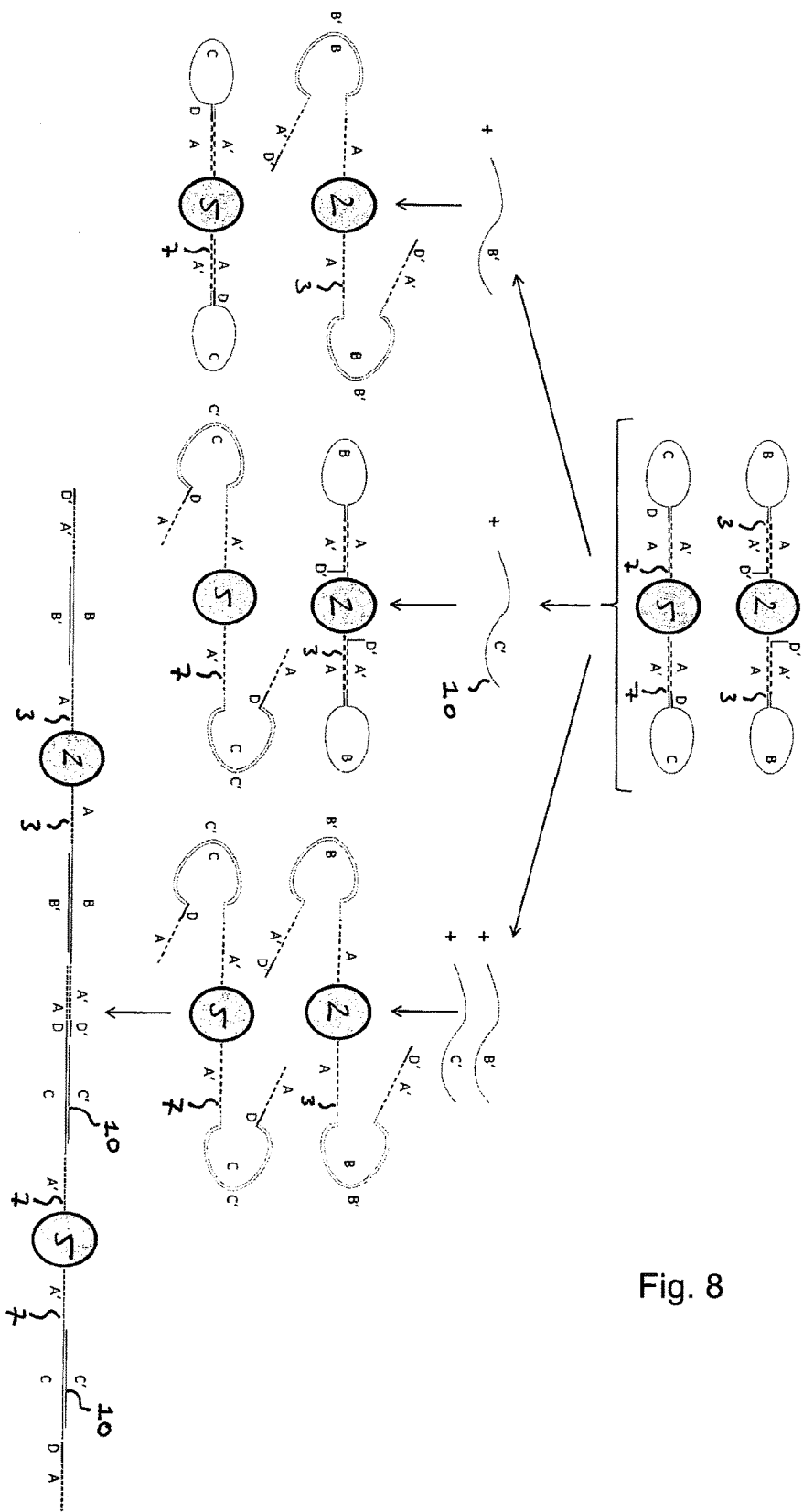
FIG. 8 a test according to the invention, in which a logic AND-function is implemented in a schematic representation.

FIG. 8 shows first probes 1 and second probes 4, which are implemented as first nanoparticles 2 and second nanoparticles 5. On the first nanoparticles 2, first oligonucleotides 3 are attached. The first oligonucleotides 3 consist of the partial sequences A, B, A', D', wherein the partial sequence A is attached to the surface of the nanoparticles 11. If a nucleic acid B' binds to the complementary part B of the first oligonucleotide 3, then the hairpin 8 opens, which results in free partial sequences A' and D'. The second nanoparticles 5 are functionalised with the second oligonucleotides 7 with the partial sequences A', C, D and A, wherein the partial sequence A' is attached to the surface of the second nanoparticle 5. If a specific nucleic acid 10 with the sequence C' hybridises with the complementary part C in the second oligonucleotide 7, the hairpin 8 of the second oligonucleotide 7 opens, which results in the partial sequences D and A becoming free. Sequence A is complementary to A' and sequence D is complementary to sequence D'. If both nucleic acids B' and C' are present in the solution, the hairpins 8 of the first oligonucleotide 3 and the second oligonucleotide 7 open, such that the first oligonucleotide 3 can hybridise with the partial sequence A and D of the second oligonucleotide 7 via the partial sequence A' and D', whereby the nanoparticles 11 are connected. Through the connection of the nanoparticles 11, a measurable change can arise, for example, a redshift and broadening of the plasmon resonance in the absorbance spectrum. If only one nucleic acid B' or C', but not both nucleic acids B' and C', are present, then the first nanoparticles 2 cannot bind to the second nanoparticles 5. In this embodiment, a logical AND-link of the two nucleic acids B' and C' is implemented, such that if and only if both nucleic acids are present in the sample at a sufficient concentration, a positive test result is generated. This can be used, for example, in diagnostic applications, in which only the simultaneous presence of two genetic features allows for a diagnostic statement on a certain medical issue.

Figure 9A:
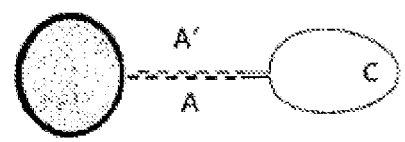
FIG. 9*a* the schematic representation of an intramolecular hairpin.
Figure 9B:
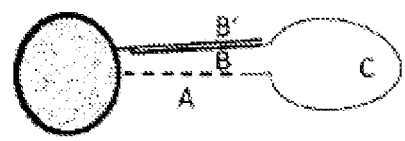
FIG. 9*b* the schematic representation of an intermolecular hairpin.

In principle, hairpins 8 on the first probes 1 and the second probes 4 can be formed in two different manners. In FIG. 9a, a conventional, so called intramolecular hairpin 8 is shown as it is used in the FIGS. 1, 3, 5, 7 and 8. Therein, the hairpin 8 consists of the arm sequences A and A' and the loop part C, wherein the partial sequence A is attached to the surface of the probe. A hybridises to the complementary part A' and forms the stem of the hairpin 8. In the presence of the nucleic acid with the sequence C', which is to be detected, this nucleic acid hybridises to the complementary loop part, whereby the hairpin 8 opens. FIG. 9b shows an intermolecular hairpin 8, wherein a short oligonucleotide 12 with the sequence B' and a long oligonucleotide 13 with the partial sequences A, C, B are attached to the surface of the probe. The long oligonucleotide 13 is attached to the surface of the probe with its partial sequence A. The partial sequence B of the long oligonucleotide 13 hybridises with the short oligonucleotide 12, such that the long oligonucleotide 13 and the short oligonucleotide 12 form a hairpin 8. In the presence of the nucleic acid with the sequence C', which is to be detected, this nucleic acid hybridises to the loop part C of the intermolecular hairpin 8, whereby the intermolecular hairpin 8 opens. Herein, the sequence B' can be identical with partial sequence A.

Figure 10:
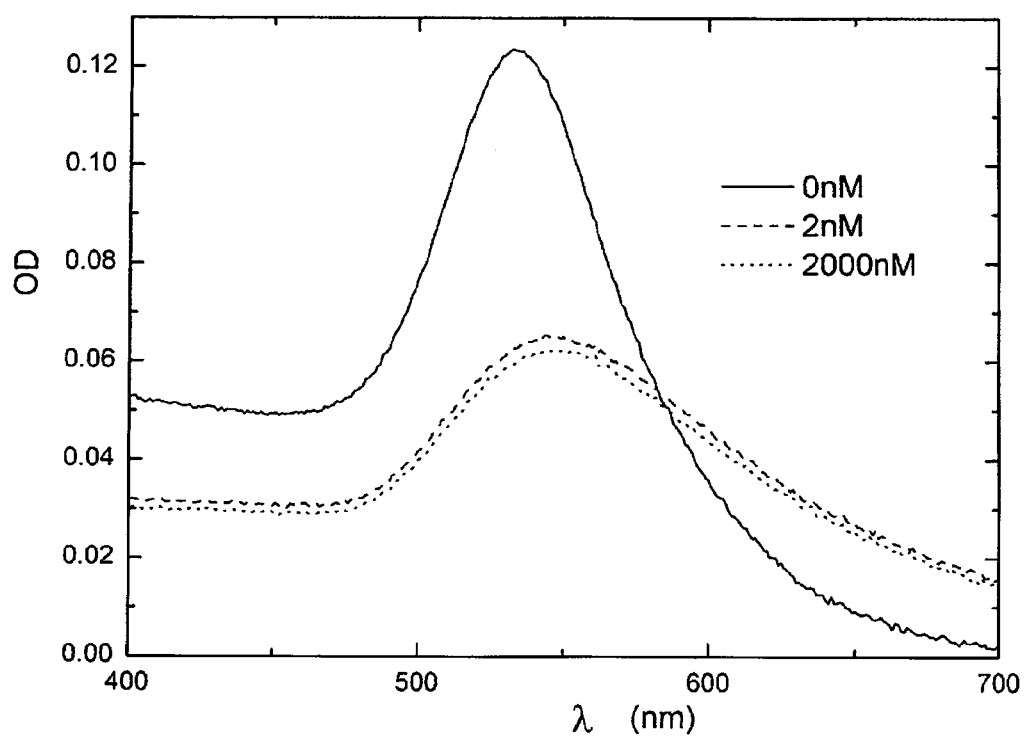
FIG. 10 three absorbance spectra of a mixture of nanoparticles in a test according to the invention in a diagram, in which the optical density (OD) is plotted against the wavelength λ in nanometers (nm)

In the embodiment of the invention in FIG. 10, the first probes 1 and the second probes 4 are implemented as in FIG. 6, also, the buffer used is the same as in FIG. 6. In the presence of the specific nucleic acid 10 with the sequence ID5, the second oligonucleotide 7, implemented as a hairpin 8, opens, whereby the first probes 1 are connected to the second probes 4 via the second oligonucleotide 7. As compared to the negative control in the absence of the specific acid 10 (continuous line), the absorbance spectrum in the presence of the specific nucleic acid 10 is clearly redshifted and broadened (dashed line) at a concentration of 2 nM. Even at a very high concentration of the specific nucleic acid 10 of 2000 nM (dotted line), the absorbance spectrum is almost unchanged as compared to the absorbance spectrum in the experiment at a concentration of the specific nucleic acid 10 of 2 nM. In this embodiment of the invention, a high concentration of the specific nucleic acid, thus, does not lead to a false negative test result.

Figure 11A:
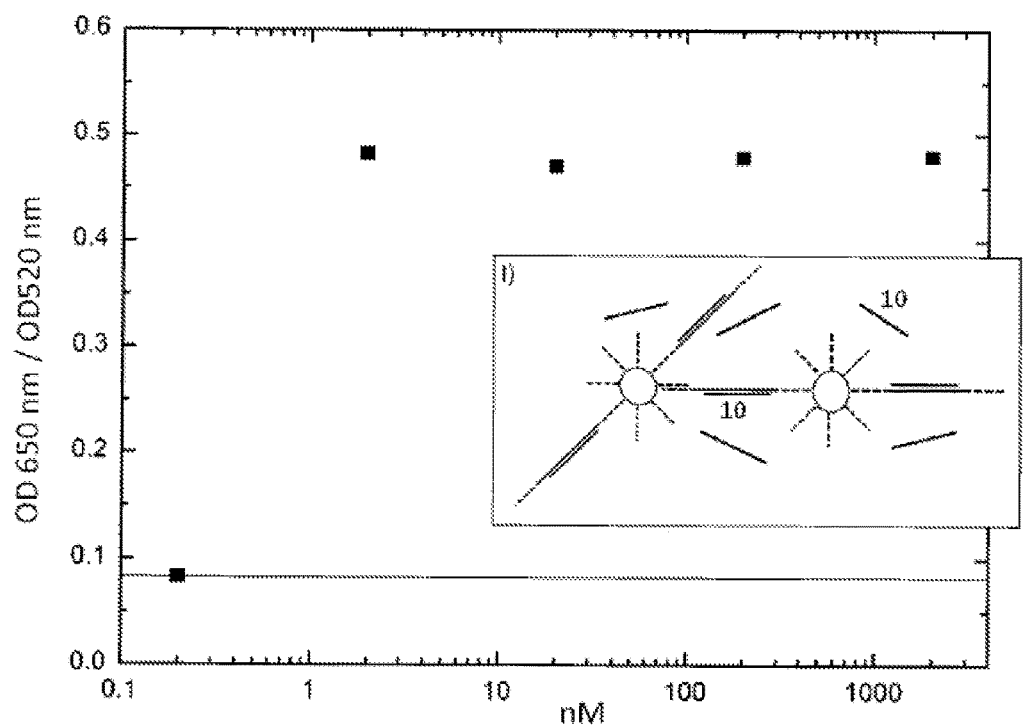
FIG. 11*a* a result of the test according to the invention from FIG. 10 as a ratio of optical density (OD) at 650 nm and optical density (OD) at 520 nm in dependence of the concentration of the specific nucleic acid; the inset (I) shows in a schematic representation that a high concentration of the specific nucleic acid does not inhibit the binding between the probes.
Figure 11B:
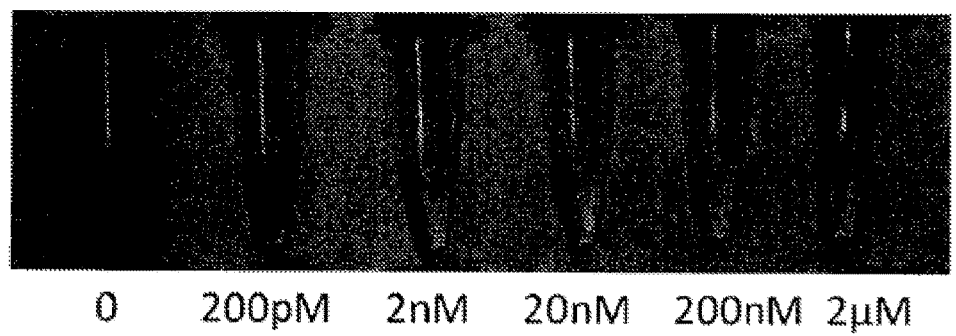
FIG. 11*b* the sample tubes of the test according to the invention from FIG. 10 with different concentrations of the specific nucleic acid.

FIGS. 11a and 11b show a further result of the experiment from FIG. 10. In FIG. 11a, the ratio of the absorbance at 650 nm and the absorbance at 520 nm is plotted against the concentration of the specific nucleic acid 10. Here, it can clearly be seen that the ratio of the absorbances, and thus the connection of the nanoparticles, at first rises with the increasing concentration of the specific nucleic acid 10, however, from a concentration of 2 nM, the ratio does not decrease again, instead, it shows a constant high degree of the connection of the nanoparticles. The inset I in FIG. 11a shows schematically the nanoparticles 2 conjugated with first oligonucleotides 3 and second nanoparticles 5 conjugated with second oligonucleotides 7 as used in this experiment. Herein, the second oligonucleotides 7 are implemented as hairpins 8 and are hybridised with specific nucleic acids 10, such that the hairpins 8 are opened and the nanoparticles 11 are connected via first oligonucleotides 3 and second oligonucleotides 7. In FIG. 11b, it is visible to the naked eye that at a concentration of the specific nucleic acid above 2 nM, the optical properties of the samples do not differ. This means at high concentrations of the specific nucleic acid no false negative test results occur. The absorbance spectra were recorded in a quartz cuvette with a 3 mm optical path and a Varian Cary 50 spectrometer.

Figure 12:
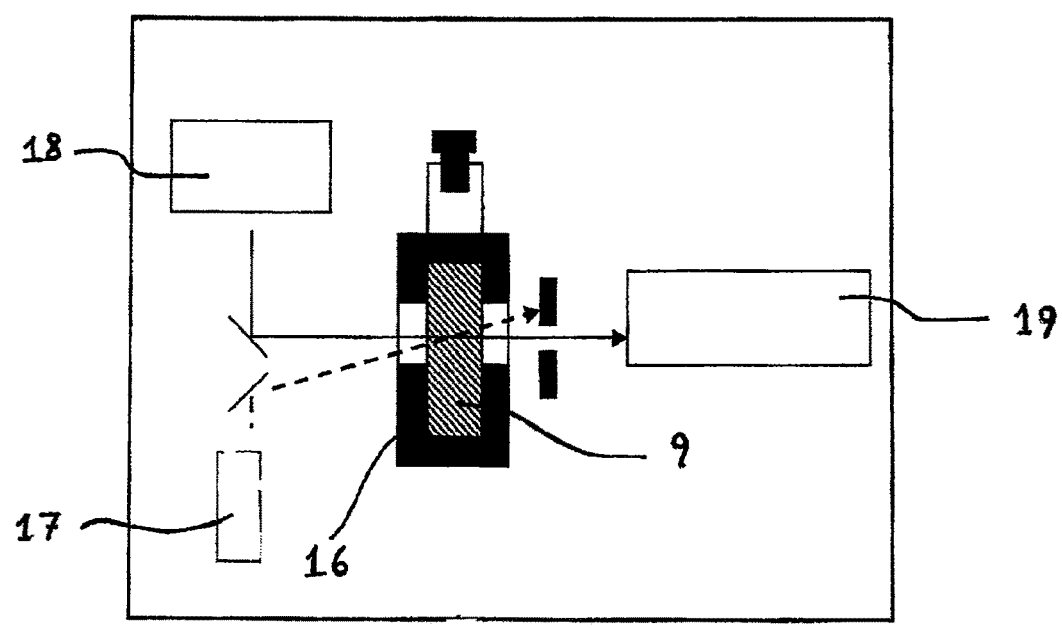
FIG. 12 an experimental setup for the application of the method according to the invention with a heating laser, a query laser and a photodiode.

FIG. 12 shows an embodiment of the invention, in which a sample container 16 with a sample 9 is contained in a cuvette; in the sample 9 nanoparticles 11 functionalised with oligonucleotides are suspended and can diffuse freely. Particularly, according to FIG. 6, nanoparticles 11 are conjugated with first oligonucleotides 3 and second oligonucleotides 7, wherein the second oligonucleotides 7 are implemented as hairpins 8. Approximately 24 hours after the addition of the specific nucleic acid 10, the nanoparticles 11 are connected to each other via opened hairpins 8. Subsequently, the nanoparticles 11 are irradiated with a light source 17, which is carried out as a heating laser 14, with laser pulses of 50 µs duration at 532 nm wavelength, approximately 700 mW peak power, focal diameter approximately 30 µm. Thereby, the nanoparticles are heated optothermically and transfer heat to the DNA, which causes the DNA to dehybridise. As a result, the nanoparticles 11, previously connected via the opened hairpins 8, are separated from each other again. This can be detected with a query laser 18, the focus of which is superimposed to the focus of the heating laser 14 and which queries the absorbance at 630 nm before and after the heating pulse. The optical path, on which the absorbance change is measured, has a length of approximately 4 mm. The intensity of the light of the query laser 18 transmitted through this layer is measured with a photodiode 19.

Figure 13:
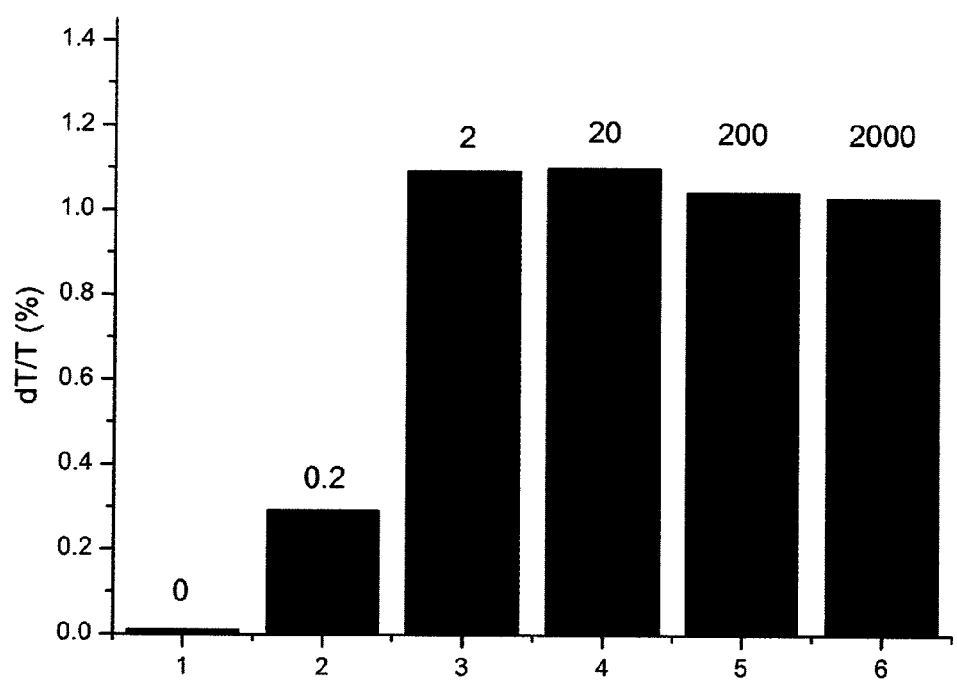
FIG. 13 the relative transmission change by an optical excitation of the nanoparticles, which leads to a heating of their surroundings, in a method according to the invention according to FIG. 12 with 6 different samples (1 to 6) with different concentrations of the specific nucleic acid (in nM)

In the embodiment of the invention in FIG. 13, the first nanoparticles 2 and the second nanoparticles 5 are implemented as in FIG. 6. Also, the buffer used is the same as in FIG. 6. FIG. 13 shows the change of the transmitted intensity of the light of the query laser 18. At first, the first nanoparticles 2 and the second nanoparticles 5 are connected via oligonucleotides on their surfaces in the presence of the specific nucleic acid 10. At this time, a first measurement of the transmission of the sample with the nanoparticles 11 is carried out. After that, the nanoparticles 11 are excited by means of a laser pulse and, as a result, are heated. Through the heating, the second oligonucleotide 7 and the specific nucleic acids 10 and/or the first oligonucleotides 3 and the second oligonucleotides 7 dehybridise, such that the nanoparticles 11 are separated. After the separation of the nanoparticles 11, the transmission is measured anew. In the absence of the specific nucleic acid 10, the nanoparticles 11 are not connected prior to the heating, such that no transmission change occurs. With an increasing concentration of the specific nucleic acid 10, the transmission change increases, wherein concentration changes of the specific nucleic acid 10 above 2 nM do not lead to a significant increase of the transmission change. Rather, from a concentration of 2 nM of the specific nucleic acid 10 onwards a plateau of the transmission change is reached. The transmission change is almost constant across three orders of magnitude of the concentration of the specific nucleic acid 10 from 2 nM to 2 mM. Even at high concentrations of the specific nucleic acid 10 no false negative test results occur in the method according to the invention.

Figure 14:
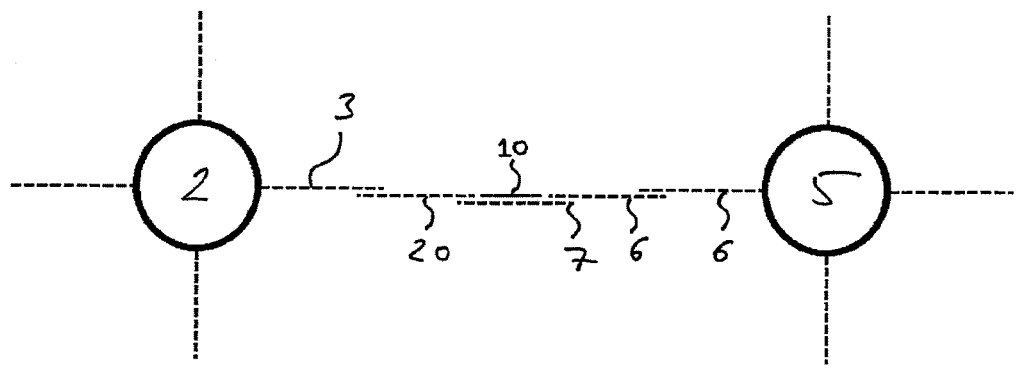
FIG. 14 a first nanoparticle, which is connected to a second nanoparticle via a first oligonucleotide, a first oligonucleotide adapter, a second oligonucleotide—which is activated by the specific nucleic acid—and via a second oligonucleotide adapter.

In FIG. 14, a first nanoparticle 2 is connected to a second nanoparticle 5 via a first oligonucleotide 3, via a first oligonucleotide adapter 20, via a second oligonucleotide 7 activated by the specific nucleic acid 10 and via the second oligonucleotide adapter 6, which consists of two parts.

Figure 15:
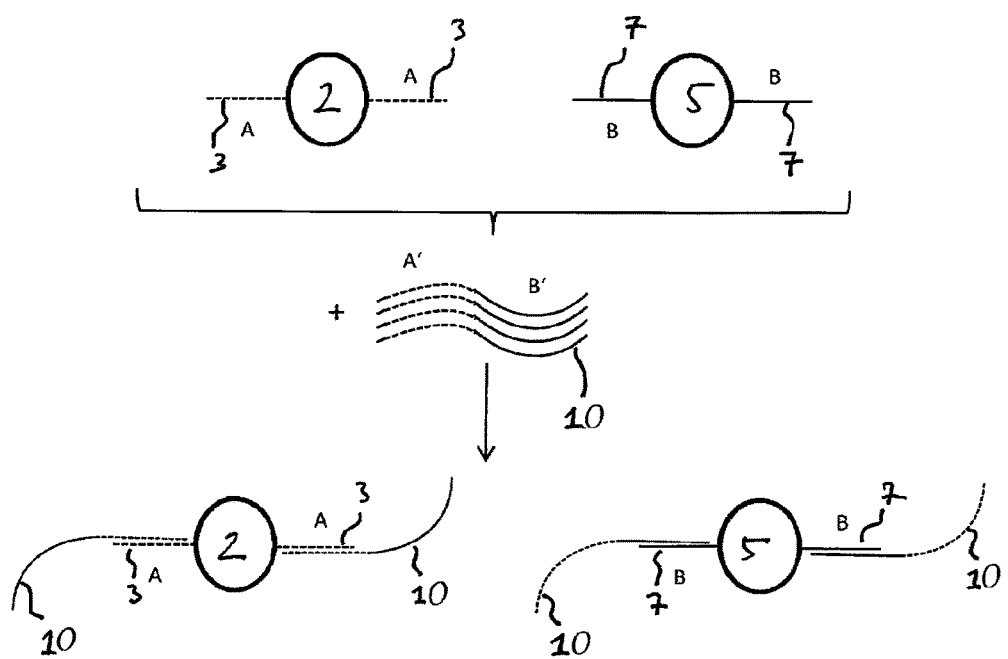
FIG. 15 in a schematic representation of the conventional test with the first and second nanoparticles and the specific nucleic acid.

In a conventional test in FIG. 15, first nanoparticles 2 are functionalised with a first oligonucleotide 3 with the sequence A and second nanoparticles 5 are functionalised with second oligonucleotides 7 with the sequence B. If a specific nucleic acid 10 to be detected with the partial sequences A' and B' is present in a solution, then the partial sequence A' of the specific nucleic acid 10 can hybridise with the first oligonucleotide 3 on the surface of the first nanoparticle 2 and the partial sequence B' of the specific nucleic acid 10 can hybridise with the second oligonucleotide 7 on the surface of the second nanoparticle 5, such that the first nanoparticle 2 is connected to the second nanoparticle 5 via the specific nucleic acid 10. Through the connection of the first nanoparticle 2 and the second nanoparticle 5, a measurable change can occur. If, however, a very high concentration of specific nucleic acids 10 is present in the sample, the predominant part of the first nanoparticles is occupied with specific nucleic acids 10 and the predominant part of the second nucleic acids 5 is also occupied with specific nucleic acids 10. For the measurable change to occur, the occupied first nanoparticles 2 need to bind to unoccupied second nanoparticles 5 and/or occupied second nanoparticles 5 need to bind to unoccupied first nanoparticles 2. As there is only a small proportion of unoccupied first nanoparticles 2 and second nanoparticles 5 present in the solution, first nanoparticles 2 and second nanoparticles 5 are not connected to a sufficient degree, such that the measurable change does not occur to a sufficient degree and the conventional test underestimates the concentration of the specific nucleic acid 10.

Figure 16:
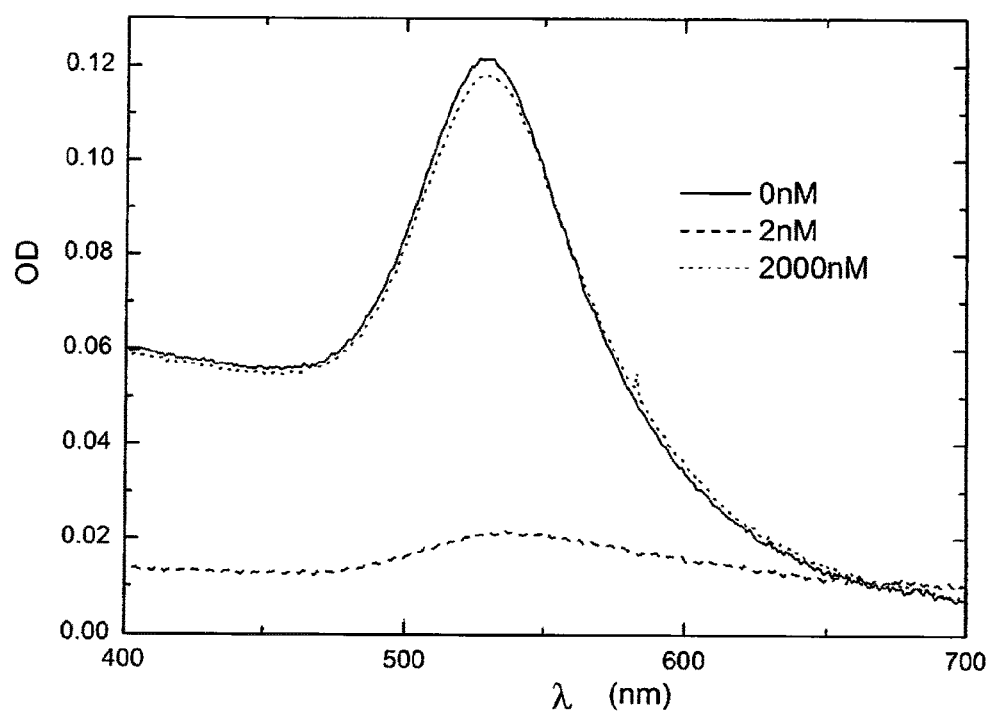
FIG. 16 three absorbance spectra of a mixture of nanoparticles in a conventional test, in which the first and second nanoparticles are connected via a specific nucleic acid present in the sample, in a diagram, in which the optical density (OD) is plotted against the wavelength λ in nanometers (nm)

The diagram in FIG. 16 shows an absorbance spectrum of a conventional test. In this test, first nanoparticles 2 and second nanoparticles 5 are present, which are implemented as nanoparticles 11 made of gold with a diameter of 60 nm. The first nanoparticles 2 are present in a solution at a concentration of 5 pM. On their surface, the first nanoparticles 2 show first oligonucleotides 3 with a sequence ID6, which is complementary to a partial sequence of the specific nucleic acid 10 to be detected. Additionally, the first nanoparticles 2 show second oligonucleotides 7 as filling sequences on their surface, which have the sequence ID3. Furthermore, second nanoparticles 5 are present in the solution at a concentration of 5 pM. On the surface of the second nanoparticles 5, third oligonucleotides 15 are attached, which have the sequence ID7 and are complementary to a further partial sequence of the specific nucleic acid 10. Additionally, second oligonucleotides 7 are attached to the surface of the second nanoparticles 5 as a filling sequence. According to the principle of the prior art (patent specification U.S. Pat. No. 6,812,334 B1, supra), the first nanoparticle 2 can bind to the second nanoparticle 5 via the first oligonucleotide 3, via the specific nucleic acid 10 and via the third oligonucleotide 15, such that a measurable change can occur. Without the specific nucleic acid 10, the absorbance spectrum shows a narrow plasmon resonance (continuous line) after approximately 24 hours. Approximately 24 hours after the addition of the specific nucleic acid 10 in a mean concentration of 2 nM with the sequence ID5 a clear redshift and broadening of the plasmon resonance in the absorbance spectrum is observed as a consequence of the connection of the particles (dashed line). In the presence of the specific nucleic acid 10 with the sequence ID5 at a high concentration of 2 mM, hardly any redshift and broadening of the plasmon resonance can be seen (dotted line). This represents a false negative result of the conventional test, which is caused by a high concentration of the nucleic acid to be detected.

Figure 17A:
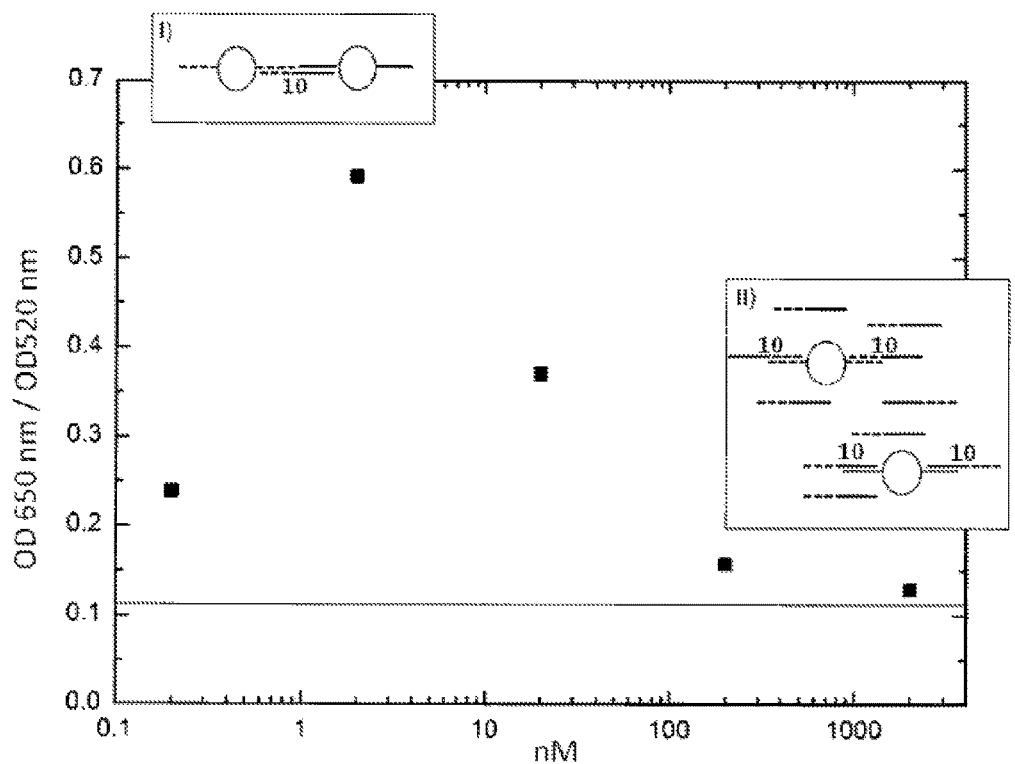
FIG. 17*a* the result of the conventional test as the ratio of the optical density (OD) at 650 nm and the optical density (OD) at 520 nm depending on the concentration of the specific nucleic acid; the inset I shows in a schematic representation the connection between the two probes via the specific nucleic acid; the inset II shows that at a high concentration, the specific nucleic acid blocks the binding of the probes to each other.
Figure 17B:
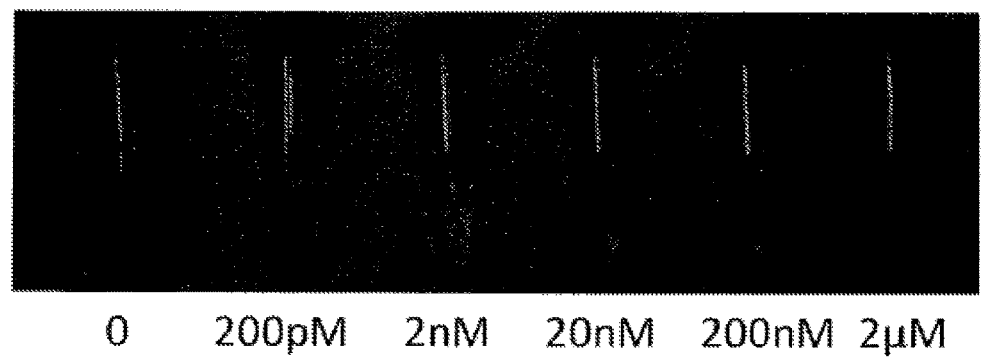
FIG. 17*b* the sample tubes of the conventional test with different concentrations of the specific nucleic acid.

FIGS. 17a and 17b show a result of the conventional test after approximately 24 hours with the experimental conditions from FIG. 16. The diagram in FIG. 17a shows the ratio of the absorbance (OD) at 650 nm and the absorbance (OD) at 520 nm depending on the concentration of the specific nucleic acid 10 to be detected in the sample 9. A broadening of the plasmon resonance, here, shows an increase of the ratio of the absorbance at 650 nm and the absorbance at 520 nm. A horizontal line is drawn as a reference value, which shows the ratio of the absorbance at 650 nm and the absorbance at 520 nm in the absence of the specific nucleic acid 10. Here, it can clearly be seen that the ratio of the absorbances and thus the nanoparticle connection at first increases with an increasing concentration, but then decreases from 2 nM when the concentration increases further. The inset I shows that at given concentration of the specific nucleic acid 10, the first nanoparticles 2 are connected to the second nanoparticles 5 via the specific nucleic acid 10. The inset II shows that at high concentrations of the specific nucleic acid 10, the oligonucleotides on the surface of the nanoparticles 11 are completely hybridised with specific nucleic acids 10, such that the nanoparticles 11 are not connected to each other anymore.

The altered optical properties are also visible with the naked eye as can be seen in FIG. 17b, which is recorded approximately 24 hours after the addition of the specific nucleic acid 10 as well. Here again, it can be observed that at intermediate concentrations of the specific nucleic acids 10 in the sample, the change of the optical properties appears most clearly. Here, high concentrations of the specific nucleic acid 10 lead to a false negative test result as well. In this embodiment of the conventional test, a buffer with 20 mM phosphate buffer and 500 mM NaCl is used. The nanoparticles 11 were functionalised according to the method of Hurst et al., supra.

In the method according to the invention as shown in FIG. 3, the disadvantages of the conventional tests are avoided, such that even at high concentrations of the specific nucleic acid 10 to be detected with the sequence C', no underestimation of the concentration of the specific nucleic acid 10 can occur. The principle difference of the invention in the embodiment of FIG. 3 as compared to the conventional test is that the specific nucleic acid 10 only needs to bind to one single oligonucleotide to cause a detectable change. In this embodiment, the specific nucleic acid 10 binds to a hairpin 8 on the surface of the second nanoparticle 5, whereby the hairpin 8 opens and the partial sequence A' is freed, which is complementary to the first oligonucleotide 3 on the surface of the first nanoparticle 2, such that the first nanoparticle 2 and the second nanoparticle 5 are connected and a measurable change occurs. This measurable change occurs even at very high concentrations of the specific nucleic acid 10 as high concentrations of the specific nucleic acid 10 cannot prevent the binding of the first nanoparticle 2 to the second nanoparticle 5.

Figure 18:
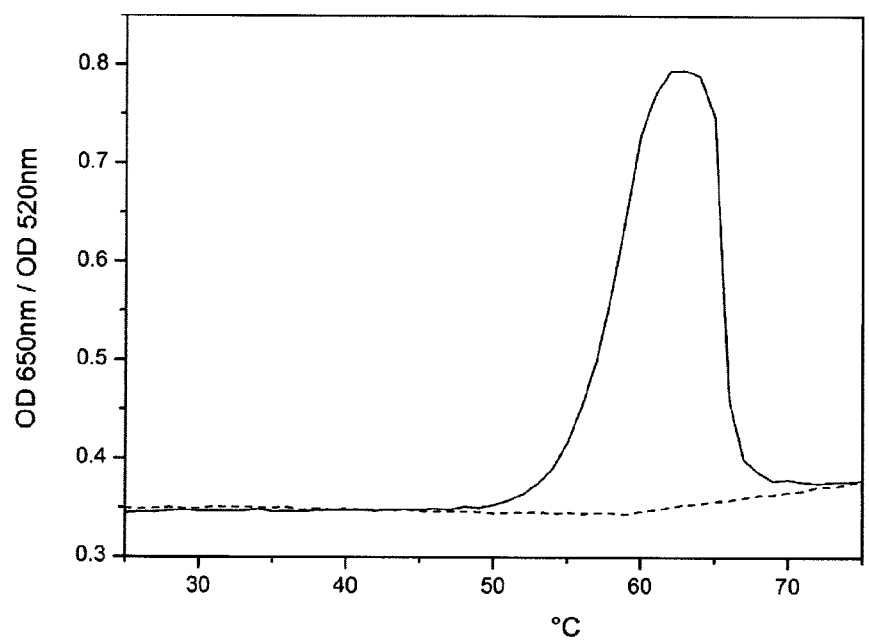
FIG. 18 the result of a test according to the invention as ratio of the optical density (OD) at 650 nm and the optical density (OD) at 520 nm depending on the hybridisation temperature with and without specific nucleic acids.

FIG. 18 shows a result of a test according to the invention as a ratio of the optical density (OD) at 650 nm and the optical density (OD) at 520 nm depending on the hybridisation temperature. The first probes 1 are implemented as nanoparticles 11 made of gold with a diameter of 20 nm and the second probes 4 are implemented as nanoparticles 11 made of gold with a diameter of 60 nm. On the surface of the first probe 1, first oligonucleotides 3 with the sequence ID3 are attached and on the surface of the second probe 4 one part second oligonucleotides with the sequence ID4 are attached and four parts oligonucleotides with the sequence ID3 are attached as a filling sequence. The concentration of the first probes is 50 pM and the concentration of the second probes 4 is 5 pM. In this experiment, the concentration of the buffer is 20 mM phosphate buffer, 500 mM NaCl. The nanoparticles were functionalised according to the method of Hurst et al., supra. The absorbance was recorded at different temperatures, wherein after each temperature increase by 1° C., a waiting period of 5 minutes before the measuring of the absorbance was observed. Without a specific nucleic acid 10, no absorbance change occurs at any temperature as the hairpin 8 is not opened. In the presence of the specific nucleic acid 10 with ID5 at a concentration of 2 nM, a significant absorbance change only occurs from a temperature of 55° C., which absorbance change shows that the hairpin 8 is opened by the specific nucleic acid 10, that the second oligonucleotide 7 has thus been activated and hybridises to the first oligonucleotide 3, which leads to a change in the distance between the first probe 1 and the second probe 4. Here, the increase temperature potentially weakens the arm sequences of the hairpins in such way that the specific nucleic acid 10 can open the hairpins 8. At a further temperature increase, the absorbance change is lost, either because the specific nucleic acid 10 and the second oligonucleotide 7 dehybridise or because first oligonucleotide 3 and second oligonucleotide 7 dehybridise. The narrow temperature window, in which the absorbance change occurs, can be of use if several different nucleic acids are to be detected in a sample. The absorbance spectra were recorded in a quartz cuvette with a 10 mm optical path and a Varian Cary 50 spectrometer.

The features disclosed in the above description, in the claims and in the drawings may be of significance, both individually and in arbitrary combination, for the realisation of the invention in its various configurations.

LIST OF REFERENCE NUMBERS 1 first probe
2 first nanoparticle
3 first oligonucleotide
4 second probe
5 second nanoparticle
6 second oligonucleotide adapter
7 second oligonucleotide
8 hairpin
9 sample
10 specific nucleic acid
11 nanoparticle
12 short oligonucleotide
13 long oligonucleotide
14 heating laser
15 third oligonucleotide
16 sample container
17 light source
18 query laser
19 photodiode
20 first oligonucleotide adapter

The invention claimed is:

1. A method for the determination of the concentration of a specific nucleic acid in a sample, wherein the sequence of the specific nucleic acid at least partially matches a reference sequence, and/or for the determination of the degree of the match of the sequence of the specific nucleic acid in a sample and a reference sequence, comprising:
   a) providing a first probe, which contains a nanoparticle and comprises a first oligonucleotide on its surface;
   b) providing a second oligonucleotide, which is partially complementary to
      i) either
         x) the first oligonucleotide or
         y) a first oligonucleotide adapter, wherein the first oligonucleotide adapter is partially complementary to the first oligonucleotide, and
      ii) the reference sequence;
      wherein the second oligonucleotide can hybridise with the specific nucleic acid in the sample, and is activated by hybridisation with the specific nucleic acid in the sample wherein the activation of the second oligonucleotide leads to the first probe being able to bind via the first oligonucleotide and—indirectly via the first oligonucleotide adapter or directly—via the second oligonucleotide to a second probe, the second probe containing a nanoparticle;
   c) combining either
      i) the first probe and the second oligonucleotide with the sample if the second oligonucleotide is partially complementary to the first oligonucleotide, or
      ii) the first probe, the second oligonucleotide and the first oligonucleotide adapter with the sample if the second oligonucleotide is partially complementary to the first oligonucleotide adapter and the first oligonucleotide adapter is partially complementary to the first oligonucleotide;
   and
   d) measuring a change of plasmon resonance of the first and second probe, which change occurs as a result of alternation of mean distance of the probes to each other due to the first probe binding to the second probe, thereby determining the concentration of the specific nucleic acid in the sample and/or determining the degree of match between the sequence of the specific nucleic acid in the sample and the reference sequence.

2. The method according to claim 1, wherein the measurable change that occurs by the activation of the second oligonucleotide occurs through the alteration of the distances of the first probes and the second probes to each other.

3. The method according to claim 1, wherein one or more of said oligonucleotides are modified with a fluorescence donor and/or a fluorescence acceptor.

4. The method according to claim 1, wherein one or more of said oligonucleotides contain a hairpin.

5. The method according to claim 1, wherein the first probe and/or the second probe comprises several different oligonucleotides on their surface.

6. The method according to claim 1, wherein two or more independent methods are carried out in the sample at the same time and the concentration of two or more different types of nucleic acids are determined by a measurement read at different temperatures.

7. The method according to claim 1, wherein the first oligonucleotide adapter and/or the second oligonucleotide adapter comprises two or more oligonucleotides, which are partially complementary to each other.

8. The method according to claim 1, wherein in addition to the second oligonucleotide, at least one further functional oligonucleotide is activated by the hybridisation with an oligonucleotide or a nucleic acid.

9. The method according to claim 8, wherein the further functional oligonucleotide is activatable by a nucleic acid B and the measurable change occurs in a logical AND-link if and only if a nucleic acid A as well as a nucleic acid B is present at a sufficient concentration in the sample.

10. The method according to claim 8, wherein binary entry values of nucleic acids in the sample are logically linked, such that a binary output value is produced according to the logic link.

11. The method according to claim 1, wherein the measurable change is determined before and after the excitation of the first probes and/or the second probes by a light source.

12. The method according to claim 1, wherein the first probe comprises two or more different oligonucleotides on its surface.

13. The method according to claim 1, wherein the measurable change is determined before and after the excitation of the first probes by a light source.

14. The method according to claim 1, wherein the binding of the first probe to the second probe involves the second oligonucleotide adapter connecting the second oligonucleotide with the second probe.

* * * * *

SEQUENCE LISTING

<160> NUMBER OF SEQ ID NOS: 8

<210> SEQ ID NO 1
<211> LENGTH: 44
<212> TYPE: DNA
<213> ORGANISM: Artificial Sequence
<220> FEATURE:
<223> OTHER INFORMATION: probe oligonucleotide ID1a

<400> SEQUENCE: 1
aaaaaaaaaa aaaaaaaaaa aaaaaaccta atgaatgtgt aatc                44

<210> SEQ ID NO 2
<211> LENGTH: 37
<212> TYPE: DNA
<213> ORGANISM: Artificial Sequence
<220> FEATURE:
<223> OTHER INFORMATION: probe oligonucleotide ID1b

<400> SEQUENCE: 2
aaaaaaaaaa aaaaaaaaaa aaaatgcaag caatcac                        37

<210> SEQ ID NO 3
<211> LENGTH: 97
<212> TYPE: DNA
<213> ORGANISM: Artificial Sequence
<220> FEATURE:
<223> OTHER INFORMATION: hairpin oligonucleotide ID2

<400> SEQUENCE: 3
gtgattgctt gcttctaatg aatgtgtaaa tgatgcgggt tgtgttaatt gagcaagtgt    60
atagagcatt taagattata gattacacat tcattag                            97

<210> SEQ ID NO 4
<211> LENGTH: 25
<212> TYPE: DNA
<213> ORGANISM: Artificial Sequence
<220> FEATURE:
<223> OTHER INFORMATION: probe oligonucleotide ID3

<400> SEQUENCE: 4
aaaaaaaaaa aaaaaaaaaa aaaaa                                     25

<210> SEQ ID NO 5
<211> LENGTH: 100
<212> TYPE: DNA
<213> ORGANISM: Artificial Sequence
<220> FEATURE:
<223> OTHER INFORMATION: probe oligonucleotide ID4

<400> SEQUENCE: 5
aaaaaaaaaa aaaaaaaaaa aaaaaaaaaa tgatgcgggt tgtgttaatt gagcaagtgt    60
atagagcatt taagattatg tttttttttt tttttttttt                        100

<210> SEQ ID NO 6
<211> LENGTH: 73
<212> TYPE: DNA
<213> ORGANISM: Artificial Sequence
<220> FEATURE:
<223> OTHER INFORMATION: hairpin binding oligonucleotide ID5

<400> SEQUENCE: 6
acgcataatc ttaaatgtctc tatacacttg ctcaattaac acaacccgca tcatttgatg    60
tgggaatgtc att                                                      73

```
<210> SEQ ID NO 7
<211> LENGTH: 36
<212> TYPE: DNA
<213> ORGANISM: Artificial Sequence
<220> FEATURE:
<223> OTHER INFORMATION: probe oligonucleotide ID6

<400> SEQUENCE: 7
aaaaaaaaaa aaaaaaaaaa aagtgtatag agcatt                                    36

<210> SEQ ID NO 8
<211> LENGTH: 33
<212> TYPE: DNA
<213> ORGANISM: Artificial Sequence
<220> FEATURE:
<223> OTHER INFORMATION: probe oligonucleotide ID7

<400> SEQUENCE: 8
aaaaaaaaaa aaaaaaaaaa gcgggttgtg tta                                       33
```